US008464288B2

(12) United States Patent
Pradeep et al.

(10) Patent No.: US 8,464,288 B2
(45) Date of Patent: *Jun. 11, 2013

(54) METHODS AND APPARATUS FOR PROVIDING PERSONALIZED MEDIA IN VIDEO

(75) Inventors: Anantha Pradeep, Berkeley, CA (US); Robert T. Knight, Berkeley, CA (US); Ramachandran Gurumoorthy, Berkeley, CA (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 535 days.

This patent is subject to a terminal disclaimer.

(21) Appl. No.: 12/357,322

(22) Filed: Jan. 21, 2009

(65) Prior Publication Data

US 2010/0186031 A1 Jul. 22, 2010

(51) Int. Cl.
*H04N 7/025* (2006.01)
*H04N 7/10* (2006.01)

(52) U.S. Cl.
USPC .............................................. 725/32; 725/34

(58) Field of Classification Search
USPC ..................................... 725/34, 32
See application file for complete search history.

(56) References Cited

U.S. PATENT DOCUMENTS

| 2,549,836 | A | 4/1951 | McIntyre et al. |
| 3,490,439 | A | 1/1970 | Rolston |
| 3,572,322 | A | 3/1971 | Wade |
| 3,735,753 | A | 5/1973 | Pisarski |
| 3,880,144 | A | 4/1975 | Coursin et al. |
| 3,901,215 | A | 8/1975 | John |
| 3,998,213 | A | 12/1976 | Price |
| 4,075,657 | A | 2/1978 | Weinblatt |
| 4,149,716 | A | 4/1979 | Scudder |
| 4,201,224 | A | 5/1980 | John |
| 4,279,258 | A | 7/1981 | John |
| 4,411,273 | A | 10/1983 | John |

(Continued)

FOREIGN PATENT DOCUMENTS

| GB | 1374658 | 11/1974 |
| GB | 2221759 | 2/1990 |

(Continued)

OTHER PUBLICATIONS

Osborne, Dominic, "Embedded Watermarking for Images Verification in Telemedicine," Thesis submitted for the degree of Doctor of Philosophy, Electrical and Electronic Engineering, University of Adelaide, 2005, 219 pages.

(Continued)

*Primary Examiner* — Mulugeta Mengesha
(74) *Attorney, Agent, or Firm* — Hanley, Flight & Zimmerman, LLC

(57) ABSTRACT

A system provides personalized media in video for presentation using a video decoder in a device such as a video recorder, hardware or software player, computer system, or television. The personalized media may be embedded or hidden in a video stream or provided separately. A video decoder determines profile and preference information associated with a viewer, group, or demographic and personalizes commercial content using the profile and preference information. The system includes personalized media by introducing, embedding, overlaying, etc., media on video during commercial breaks. Personalized media may be provided during normal viewing or may be provided when a skip forward or fast forward request is received. The system may also evaluate personalization mechanisms using neuro-response measurements.

46 Claims, 11 Drawing Sheets

U.S. PATENT DOCUMENTS

| | | | |
|---|---|---|---|
| 4,417,592 A | 11/1983 | John | |
| 4,537,198 A | 8/1985 | Corbett | |
| 4,557,270 A | 12/1985 | John | |
| 4,610,259 A | 9/1986 | Cohen et al. | |
| 4,613,951 A | 9/1986 | Chu | |
| 4,632,122 A | 12/1986 | Johansson et al. | |
| 4,683,892 A | 8/1987 | Johansson et al. | |
| 4,695,879 A | 9/1987 | Weinblatt | |
| 4,736,751 A | 4/1988 | Gevins et al. | |
| 4,800,888 A | 1/1989 | Itil et al. | |
| 4,802,484 A | 2/1989 | Friedman et al. | |
| 4,846,190 A | 7/1989 | John | |
| 4,885,687 A | 12/1989 | Carey | |
| 4,894,777 A | 1/1990 | Negishi et al. | |
| 4,913,160 A | 4/1990 | John | |
| 4,955,388 A | 9/1990 | Silberstein | |
| 4,967,038 A | 10/1990 | Gevins et al. | |
| 4,987,903 A | 1/1991 | Keppel et al. | |
| 5,003,986 A | 4/1991 | Finitzo et al. | |
| 5,038,782 A | 8/1991 | Gevins et al. | |
| 5,052,401 A | 10/1991 | Sherwin | |
| 5,083,571 A | 1/1992 | Prichep | |
| RE34,015 E | 8/1992 | Duffy | |
| 5,137,027 A | 8/1992 | Rosenfeld | |
| 5,213,338 A | 5/1993 | Brotz | |
| 5,226,177 A | 7/1993 | Nickerson | |
| 5,243,517 A | 9/1993 | Schmidt et al. | |
| 5,291,888 A | 3/1994 | Tucker | |
| 5,293,867 A | 3/1994 | Oommen | |
| 5,295,491 A | 3/1994 | Gevins | |
| 5,339,826 A | 8/1994 | Schmidt et al. | |
| 5,357,957 A | 10/1994 | Itil et al. | |
| 5,363,858 A | 11/1994 | Farwell | |
| 5,392,788 A | 2/1995 | Hudspeth | |
| 5,406,956 A | 4/1995 | Farwell | |
| 5,447,166 A | 9/1995 | Gevins | |
| 5,474,082 A | 12/1995 | Junker | |
| 5,479,934 A | 1/1996 | Imran | |
| 5,518,007 A | 5/1996 | Becker | |
| 5,537,618 A | 7/1996 | Boulton et al. | |
| 5,617,855 A | 4/1997 | Waletzky et al. | |
| 5,655,534 A | 8/1997 | Ilmoniemi | |
| 5,676,138 A | 10/1997 | Zawilinski | |
| 5,720,619 A | 2/1998 | Fisslinger | |
| 5,724,987 A | 3/1998 | Gevins et al. | |
| 5,729,205 A | 3/1998 | Kwon | |
| 5,762,611 A | 6/1998 | Lewis et al. | |
| 5,771,897 A | 6/1998 | Zufrin | |
| 5,787,187 A | 7/1998 | Bouchard et al. | |
| 5,800,351 A | 9/1998 | Mann | |
| 5,812,642 A | 9/1998 | Leroy | |
| 5,817,029 A | 10/1998 | Gevins et al. | |
| 5,848,399 A | 12/1998 | Burke | |
| 5,945,863 A | 8/1999 | Coy | |
| 5,961,332 A | 10/1999 | Joao | |
| 5,983,129 A | 11/1999 | Cowan et al. | |
| 6,001,065 A | 12/1999 | DeVito | |
| 6,021,346 A | 2/2000 | Ryu et al. | |
| 6,052,619 A | 4/2000 | John | |
| 6,099,319 A * | 8/2000 | Zaltman et al. | 434/236 |
| 6,120,440 A | 9/2000 | Goknar | |
| 6,128,521 A | 10/2000 | Marro et al. | |
| 6,154,669 A | 11/2000 | Hunter et al. | |
| 6,161,030 A | 12/2000 | Levendowski et al. | |
| 6,173,260 B1 | 1/2001 | Slaney | |
| 6,175,753 B1 | 1/2001 | Menkes et al. | |
| 6,228,038 B1 | 5/2001 | Claessens | |
| 6,236,885 B1 | 5/2001 | Hunter et al. | |
| 6,254,536 B1 | 7/2001 | DeVito | |
| 6,280,198 B1 | 8/2001 | Calhoun et al. | |
| 6,286,005 B1 | 9/2001 | Cannon | |
| 6,289,234 B1 | 9/2001 | Mueller | |
| 6,292,688 B1 | 9/2001 | Patton | |
| 6,301,493 B1 | 10/2001 | Marro et al. | |
| 6,315,569 B1 | 11/2001 | Zaltman | |
| 6,330,470 B1 | 12/2001 | Tucker et al. | |
| 6,334,778 B1 | 1/2002 | Brown | |
| 6,374,143 B1 | 4/2002 | Berrang et al. | |
| 6,381,481 B1 | 4/2002 | Levendowski et al. | |
| 6,398,643 B1 | 6/2002 | Knowles et al. | |
| 6,422,999 B1 | 7/2002 | Hill | |
| 6,434,419 B1 | 8/2002 | Gevins et al. | |
| 6,453,194 B1 | 9/2002 | Hill | |
| 6,487,444 B2 | 11/2002 | Mimura | |
| 6,488,617 B1 | 12/2002 | Katz | |
| 6,510,340 B1 | 1/2003 | Jordan | |
| 6,520,905 B1 | 2/2003 | Surve et al. | |
| 6,545,685 B1 * | 4/2003 | Dorbie | 345/582 |
| 6,575,902 B1 | 6/2003 | Burton et al. | |
| 6,577,329 B1 | 6/2003 | Flickner et al. | |
| 6,585,521 B1 | 7/2003 | Obrador | |
| 6,594,521 B2 | 7/2003 | Tucker | |
| 6,598,006 B1 | 7/2003 | Honda et al. | |
| 6,654,626 B2 | 11/2003 | Devlin et al. | |
| 6,662,052 B1 | 12/2003 | Sarwal et al. | |
| 6,665,560 B2 | 12/2003 | Becker et al. | |
| 6,688,890 B2 | 2/2004 | von Buegner | |
| 6,708,051 B1 | 3/2004 | Durousseau | |
| 6,712,468 B1 | 3/2004 | Edwards | |
| 6,754,524 B2 | 6/2004 | Johnson, Jr. | |
| 6,757,556 B2 | 6/2004 | Gopenathan et al. | |
| 6,788,882 B1 | 9/2004 | Geer et al. | |
| 6,792,304 B1 | 9/2004 | Silberstein | |
| 6,842,877 B2 | 1/2005 | Robarts et al. | |
| 6,904,408 B1 | 6/2005 | McCarthy et al. | |
| 6,950,698 B2 | 9/2005 | Sarkela et al. | |
| 6,973,342 B1 | 12/2005 | Swanson | |
| 6,993,380 B1 | 1/2006 | Modarres | |
| 7,120,880 B1 | 10/2006 | Dryer et al. | |
| 7,130,673 B2 | 10/2006 | Tolvanen-Laakso et al. | |
| 7,150,715 B2 | 12/2006 | Collura et al. | |
| 7,164,967 B2 | 1/2007 | Etienne-Cummings et al. | |
| 7,177,675 B2 | 2/2007 | Suffin et al. | |
| 7,286,871 B2 | 10/2007 | Cohen | |
| 7,340,060 B2 | 3/2008 | Tomkins et al. | |
| 7,391,835 B1 | 6/2008 | Gross et al. | |
| 7,496,400 B2 | 2/2009 | Hoskonen et al. | |
| 7,548,774 B2 | 6/2009 | Kurtz et al. | |
| 7,551,952 B2 | 6/2009 | Gevins et al. | |
| 7,623,823 B2 | 11/2009 | Zito et al. | |
| 7,636,456 B2 | 12/2009 | Collins et al. | |
| 7,689,272 B2 | 3/2010 | Farwell | |
| 7,697,979 B2 | 4/2010 | Martinerie et al. | |
| 7,698,238 B2 | 4/2010 | Barletta et al. | |
| 7,720,351 B2 | 5/2010 | Levitan | |
| 7,729,755 B2 | 6/2010 | Laken | |
| 7,809,420 B2 | 10/2010 | Hannula et al. | |
| 7,840,248 B2 | 11/2010 | Fuchs et al. | |
| 7,840,250 B2 | 11/2010 | Tucker | |
| 7,865,394 B1 * | 1/2011 | Calloway et al. | 705/14.4 |
| 7,892,764 B2 | 2/2011 | Xiong et al. | |
| 7,917,366 B1 | 3/2011 | Levanon et al. | |
| 7,988,557 B2 | 8/2011 | Soderland | |
| 8,014,847 B2 | 9/2011 | Shastri et al. | |
| 8,069,125 B2 | 11/2011 | Jung et al. | |
| 8,082,215 B2 | 12/2011 | Jung et al. | |
| 8,086,563 B2 | 12/2011 | Jung et al. | |
| 8,103,328 B2 | 1/2012 | Turner et al. | |
| 8,209,224 B2 | 6/2012 | Pradeep et al. | |
| 8,270,814 B2 | 9/2012 | Pradeep et al. | |
| 2001/0020236 A1 | 9/2001 | Cannon | |
| 2001/0056225 A1 | 12/2001 | DeVito | |
| 2002/0065826 A1 | 5/2002 | Bell et al. | |
| 2002/0072952 A1 | 6/2002 | Hamzey et al. | |
| 2002/0077534 A1 | 6/2002 | DuRousseau | |
| 2002/0155878 A1 | 10/2002 | Lert, Jr. et al. | |
| 2002/0156842 A1 * | 10/2002 | Signes et al. | 709/203 |
| 2002/0188216 A1 | 12/2002 | Kayyali et al. | |
| 2002/0188217 A1 | 12/2002 | Farwell | |
| 2002/0193670 A1 | 12/2002 | Garfield et al. | |
| 2003/0013981 A1 | 1/2003 | Gevins et al. | |
| 2003/0036955 A1 | 2/2003 | Tanaka et al. | |
| 2003/0059750 A1 | 3/2003 | Bindler et al. | |
| 2003/0073921 A1 | 4/2003 | Sohmer et al. | |
| 2003/0100998 A2 | 5/2003 | Brunner et al. | |
| 2003/0104865 A1 | 6/2003 | Itkis et al. | |
| 2003/0165270 A1 | 9/2003 | Endrikhovski et al. | |

| | | |
|---|---|---|
| 2003/0172376 A1 | 9/2003 | Coffin, III |
| 2003/0233278 A1 | 12/2003 | Marshall |
| 2004/0005143 A1 | 1/2004 | Tsuru et al. |
| 2004/0015608 A1 | 1/2004 | Ellis et al. |
| 2004/0073129 A1* | 4/2004 | Caldwell et al. .............. 600/544 |
| 2004/0092809 A1 | 5/2004 | DeCharms |
| 2004/0098298 A1 | 5/2004 | Yin |
| 2004/0187167 A1 | 9/2004 | Maguire et al. |
| 2004/0210159 A1 | 10/2004 | Kibar et al. |
| 2004/0220483 A1 | 11/2004 | Yeo et al. |
| 2005/0010475 A1 | 1/2005 | Perkowski et al. |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0143629 A1 | 6/2005 | Farwell |
| 2005/0154290 A1 | 7/2005 | Langleben |
| 2005/0177058 A1 | 8/2005 | Sobell |
| 2005/0197590 A1 | 9/2005 | Osorio et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0273017 A1 | 12/2005 | Gordon |
| 2005/0288954 A1 | 12/2005 | McCarthy et al. |
| 2005/0289582 A1 | 12/2005 | Tavares et al. |
| 2006/0035707 A1 | 2/2006 | Nguyen et al. |
| 2006/0093998 A1 | 5/2006 | Vertegaal |
| 2006/0111644 A1 | 5/2006 | Guttag et al. |
| 2006/0129458 A1 | 6/2006 | Maggio |
| 2006/0167376 A1 | 7/2006 | Viirre et al. |
| 2006/0168630 A1* | 7/2006 | Davies ............................ 725/89 |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0293921 A1 | 12/2006 | McCarthy et al. |
| 2007/0048707 A1 | 3/2007 | Caamano et al. |
| 2007/0055169 A1 | 3/2007 | Lee et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0078706 A1 | 4/2007 | Datta et al. |
| 2007/0079331 A1 | 4/2007 | Datta et al. |
| 2007/0106170 A1 | 5/2007 | Dunseath, Jr. et al. |
| 2007/0135727 A1 | 6/2007 | Virtanen et al. |
| 2007/0225585 A1 | 9/2007 | Washbon et al. |
| 2007/0225674 A1 | 9/2007 | Molnar et al. |
| 2007/0235716 A1 | 10/2007 | Delic et al. |
| 2007/0238945 A1 | 10/2007 | Delic et al. |
| 2007/0250846 A1 | 10/2007 | Swix et al. |
| 2007/0265507 A1 | 11/2007 | de Lemos |
| 2008/0001600 A1 | 1/2008 | deCharms |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0081961 A1 | 4/2008 | Westbrook et al. |
| 2008/0082019 A1 | 4/2008 | Ludving et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0147488 A1 | 6/2008 | Tunick et al. |
| 2008/0152300 A1 | 6/2008 | Knee et al. |
| 2008/0208072 A1 | 8/2008 | Fadem et al. |
| 2008/0214902 A1 | 9/2008 | Lee et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1* | 9/2008 | Lee et al. ........................ 725/10 |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0083129 A1 | 3/2009 | Pradeep et al. |
| 2009/0088610 A1 | 4/2009 | Lee et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0112077 A1 | 4/2009 | Nguyen et al. |
| 2009/0131764 A1 | 5/2009 | Lee et al. |
| 2009/0133047 A1* | 5/2009 | Lee et al. ........................ 725/10 |
| 2009/0150919 A1 | 6/2009 | Lee et al. |
| 2009/0158308 A1 | 6/2009 | Weitzenfeld et al. |
| 2009/0163777 A1 | 6/2009 | Jung |
| 2009/0195392 A1 | 8/2009 | Zalewski |
| 2009/0214060 A1 | 8/2009 | Chuang et al. |
| 2009/0248496 A1 | 10/2009 | Hueter et al. |
| 2009/0253996 A1 | 10/2009 | Lee et al. |
| 2009/0259137 A1 | 10/2009 | Delic et al. |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0041962 A1 | 2/2010 | Causevic et al. |
| 2010/0060300 A1 | 3/2010 | Muller et al. |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0183279 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0257052 A1 | 10/2010 | Zito et al. |
| 2010/0274152 A1 | 10/2010 | McPeck et al. |
| 2010/0274153 A1 | 10/2010 | Tucker et al. |
| 2010/0325660 A1 | 12/2010 | Holden |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0059422 A1 | 3/2011 | Masaoka |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0144519 A1 | 6/2011 | Causevic |
| 2011/0224569 A1 | 9/2011 | Isenhart et al. |
| 2011/0237971 A1 | 9/2011 | Pradeep et al. |

| | | | |
|---|---|---|---|
| 2011/0248729 | A2 | 10/2011 | Mueller et al. |
| 2011/0270620 | A1 | 11/2011 | Pradeep et al. |
| 2011/0276504 | A1 | 11/2011 | Pradeep et al. |
| 2011/0282231 | A1 | 11/2011 | Pradeep et al. |
| 2011/0282232 | A1 | 11/2011 | Pradeep et al. |
| 2011/0282749 | A1 | 11/2011 | Pradeep et al. |
| 2011/0319975 | A1 | 12/2011 | Ho et al. |
| 2012/0036004 | A1 | 2/2012 | Pradeep et al. |
| 2012/0036005 | A1 | 2/2012 | Pradeep et al. |
| 2012/0054018 | A1 | 3/2012 | Pradeep et al. |
| 2012/0072289 | A1 | 3/2012 | Pradeep et al. |
| 2012/0108995 | A1 | 5/2012 | Pradeep et al. |
| 2012/0114305 | A1 | 5/2012 | Holden |
| 2012/0130800 | A1 | 5/2012 | Pradeep et al. |
| 2012/0301120 | A1 | 11/2012 | Pradeep et al. |

FOREIGN PATENT DOCUMENTS

| | | |
|---|---|---|
| WO | 97/17774 | 5/1997 |
| WO | 97/40745 | 11/1997 |
| WO | 97/41673 | 11/1997 |
| WO | 2004/049225 | 6/2004 |
| WO | 2008077178 | 7/2008 |
| WO | 2008-109694 | 9/2008 |
| WO | 2008-109699 | 9/2008 |
| WO | 2008/121651 | 10/2008 |
| WO | 2008/137579 | 11/2008 |
| WO | 2008/154410 | 12/2008 |
| WO | 2009/018374 | 2/2009 |
| WO | 2009/052833 | 4/2009 |

OTHER PUBLICATIONS

Barcelo, Francisco, et al., "Prefrontal Modulation of Visual Processing in Humans," Nature Neuroscience, vol. 3, No. 4, Apr. 2000, pp. 399-403.

Canolty, R.T., et al., "High Gamma Power Is Phase-Locked to Theta Oscillations in Human Neocortex," Science, vol. 313, Sep. 15, 2006, pp. 1626-1628.

Engel, Andreas, et al., "Dynamic Predictions: Oscillations and Synchrony in Top-Down Processing," Macmillan Magazines Ltd, vol. 2, Oct. 2001, pp. 704-716.

Fries, Pascal, "A Mechanism for Cognitive Dynamics: Neuronal Communication Through Neuronal Coherence," TRENDS in Cognitive Sciences, vol. 9, No. 10, Oct. 2005, p. 474-480.

Gazzaley, Adam, et al., "Top-down Enhancement and Suppression of the Magnitude and Speed of Neural Activity," Journal of Cognitive Neuroscience, vol. 17, No. 3, pp. 507-517.

Hartikainen, Kaisa, et al., "Emotionally Arousing Stimuli Compete with Attention to Left Hemispace," Editorial Manager(tm) for NeuroReport, Manuscipt Draft, Manuscript No. NR-D-07-5935R1, submitted Sep. 8, 2007, 26 pages.

Knight, Robert T., "Contribution of Human Hippocampal Region to Novelty Detection," Nature, vol. 383, Sep. 19, 1996, p. 256-259.

Knight Robert T., "Decreased Response to Novel Stimuli After Prefrontal Lesions in Man," Electroencephalography and Clinical Neurophysiology, vol. 59, 1984, pp. 9-20.

Miltner, Wolfgang H.R., et al., "Coherence of Gamma-band EEG Activity as a Basis for Associative Learning," Nature, vol. 397, Feb. 4, 1999, pp. 434-436.

Final Rejection, issued by the United States Patent and Trademark Office in connection with U.S. Appl. No. 12/056,211, on Jul. 8, 2011, 16 pages.

Office Action, issued by the United States Patent and Trademark Office in connection with U.S. Appl. No. 12/056,211, on Jan. 7, 2011, 19 pages.

Office Action issued by the United States Patent and Trademark Office in connection with U.S. Appl. No. 12/056,221, on Apr. 15, 2011, 24 pages.

Final Rejection, issued by the United States Patent and Trademark Office in connection with U.S. Appl. No. 12/113,863, on Jun. 9, 2011, 12 pages.

Office Action, issued by the United States Patent and Trademark Office in connection with U.S. Appl. No. 12/113,863, on Dec. 27, 2010, 15 pages.

Final Rejection, issued by the United States Patent and Trademark Office in connection with U.S. Appl. No. 12/113,870, on Apr. 21, 2011, 10 pages.

Office Action, issued by the United States Patent and Trademark Office in connection with U.S. Appl. No. 12/113,870, on Dec. 3, 2010, 12 pages.

Office Action, issued by the United States Patent and Trademark Office in connection with U.S. Appl. No. 12/122,240, on Jun. 10, 2011, 12 pages.

Final Rejection, issued by the United States Patent and Trademark Office in connection with U.S. Appl. No. 12/122,262, on May 26, 2011, 15 pages.

Office Action, issued by the United States Patent and Trademark Office in connection with U.S. Appl. No. 12/122,262, on Dec. 9, 2010, 13 pages.

Final Rejection, issued by the United States Patent and Trademark Office in connection with U.S. Appl. No. 12/135,066, on Jan. 21, 2011, 16 pages.

Office Action, issued by the United States Patent and Trademark Office in connection with U.S. Appl. No. 12/135,066, on Oct. 28, 2010, 14 pages.

Notice of Panel Decision from Pre-Appeal Brief Review, issued by the United States Patent and Trademark Office in connection with U.S. Appl. No. 12/135,066, on May 31, 2011, 2 pages.

Office Action, issued by the United States Patent and Trademark Office in connection with U.S. Appl. No. 12/135,074, on Dec. 23, 2010, 14 pages.

Final Rejection, issued by the United States Patent and Trademark Office in connection with U.S. Appl. No. 12/135,074, on Jun. 9, 2011, 10 pages.

Final Rejection, issued by the United States Patent and Trademark Office in connection with U.S. Appl. No. 12/182,874, on Jul. 7, 2011, 14 pages.

Office Action, issued by the United States Patent and Trademark Office in connection with U.S. Appl. No. 12/182,874, on Dec. 27, 2010, 17 pages.

Office Action, issued by the United States Patent and Trademark Office in connection with U.S. Appl. No. 12/199,557, on Dec. 27, 2010, 14 pages.

Final Rejection, issued by the United States Patent and Trademark Office in connection with U.S. Appl. No. 12/199,557, on Jun. 9, 2011, 12 pages.

Final Rejection, issued by the United States Patent and Trademark Office in connection with U.S. Appl. No. 12/199,583, on Jun. 21, 2011, 14 pages.

Office Action, issued by the United States Patent and Trademark Office in connection with U.S. Appl. No. 12/199,583, on Dec. 27, 2010, 17 pages.

Final Rejection, issued by the United States Patent and Trademark Office in connection with U.S. Appl. No. 12/199,596, on Jun. 14, 2011, 13 pages.

Office Action, issued by the United States Patent and Trademark Office in connection with U.S. Appl. No. 12/199,596, on Dec. 27, 2010, 17 pages.

Final Rejection, issued by the United States Patent and Trademark Office in connection with U.S. Appl. No. 12/200,813, on Jul. 6, 2011, 13 pages.

Office Action, issued by the United States Patent and Trademark Office in connection with U.S. Appl. No. 12/200,813, on Dec. 27, 2010, 14 pages.

Office Action, issued by the United States Patent and Trademark Office in connection with U.S. Appl. No. 12/234,372, on Jun. 7, 2011, 10 pages.

Final Rejection, issued by the United States Patent and Trademark Office in connection with U.S. Appl. No. 12/135,069, on Feb. 17, 2011, 32 pages.

Office Action, issued by the United States Patent and Trademark Office in connection with U.S. Appl. No. 12/135,069, on Oct. 29, 2010, 21 pages.

Office Action, issued by the United States Patent and Trademark Office in connection with U.S. Appl. No. 12/357,315, on May 4, 2011, 9 pages.

Office Action, issued by the United States Patent and Trademark Office in connection with U.S. Appl. No. 12/410,380, on Jun. 7, 2011, 9 pages.
Office Action, issued by the United States Patent and Trademark Office in connection with U.S. Appl. No. 12/413,297, on Jul. 18, 2011, 9 pages.
Office Action, issued by the United States Patent and Trademark Office in connection with U.S. Appl. No. 12/608,685, on Jul. 12, 2011, 15 pages.
Office Action, issued by the United States Patent and Trademark Office in connection with U.S. Appl. No. 12/056,190, on Aug. 10, 2011, 28 pages.
Office Action, issued by the United States Patent and Trademark Office in connection with U.S. Appl. No. 12/135,069, on Aug. 26, 2011, 33 pages.
Restriction Requirement, issued by the United States Patent and Trademark Office in connection with U.S. Appl. No. 12/122,253, on Sep. 2, 2011, 7 pages.
Office Action, issued by the United States Patent and Trademark Office in connection with U.S. Appl. No. 12/410,372, on Sep. 12, 2011, 12 pages.
Restriction Requirement, issued by the United States Patent and Trademark Office in connection with U.S. Appl. No. 12/182,851, on Sep. 12, 2011, 7 pages.
International Preliminary Report on Patentability, issued by the International Bureau of WIPO in connection with International Application No. PCT/US08/058264, on Sep. 29, 2009, 1 page.
International Search Report, issued by the International Searching Authority in connection with International Application No. PCT/US08/058264, on Aug. 1, 2008, 2 pages.
Written Opinion, issued by the International Searching Authority in connection with International Application No. PCT/US08/058264, on Aug. 1, 2008, 5 pages.
International Preliminary Report on Patentability, issued by the International Bureau of WIPO in connection with International Application No. PCT/US08/062273, on Nov. 3, 2009, 1 page.
International Search Report, issued by the International Searching Authority in connection with International Application No. PCT/US08/062273, on Sep. 5, 2008, 2 pages.
Written Opinion, issued by the International Searching Authority in connection with International Application No. PCT/US08/062273, on Sep. 5, 2008, 4 pages.
International Preliminary Report on Patentability, issued by the International Bureau of WIPO in connection with International Application No. PCT/US08/062275, on Nov. 3, 2009, 1 page.
International Search Report, issued by the International Bureau in connection with International Application No. PCT/US08/062275, on Sep. 22, 2008, 2 pages.
Written Opinion, issued by the International Bureau in connection with International Application No. PCT/US08/062275, on Sep. 22, 2008, 6 pages.
International Preliminary Report on Patentability, issued by the International Bureau of WIPO in connection with International Application No. PCT/US08/063984, on Nov. 17, 2009, 1 page.
International Search Report, issued by the International Bureau in connection with International Application No. PCT/US08/063984, on Sep. 29, 2008, 3 pages.
Written Opinion, issued by the International Bureau in connection with International Application No. PCT/US08/063984, on Sep. 29, 2008, 4 pages.
International Preliminary Report on Patentability, issued by the International Bureau of WIPO in connection with International Application No. PCT/US08/063989, on Nov. 17, 2009, 1 page.
International Search Report, issued by the International Bureau in connection with International Application No. PCT/US08/063989, on Jul. 17, 2008, 2 pages.
Written Opinion, issued by the International Bureau in connection with International Application No. PCT/US08/063989, on Jul. 17, 2008, 4 pages.
International Preliminary Report on Patentability, issued by the International Bureau of WIPO in connection with International Application No. PCT/US08/066166, on Dec. 7, 2009, 1 page.
International Search Report, issued by the International Bureau in connection with International Application No. PCT/US08/066166, on Aug. 25, 2008, 2 pages.
Written Opinion, issued by the International Bureau in connection with International Application No. PCT/US08/066166, on Aug. 25, 2008, 6 pages.
International Preliminary Report on Patentability, issued by the International Bureau of WIPO in connection with International Application No. PCT/US08/071639, on Feb. 2, 2010, 1 page.
International Search Report, issued by the International Bureau in connection with International Application No. PCT/US08/071639, on Oct. 22, 2008, 3 pages.
Written Opinion, issued by the International Bureau in connection with International Application No. PCT/US08/071639, on Oct. 22, 2008, 4 pages.
International Preliminary Report on Patentability, issued by the International Bureau of WIPO in connection with International Application No. PCT/US08/074467, on Mar. 2, 2010, 1 page.
International Search Report, issued by the International Bureau in connection with International Application No. PCT/US08/074467, on Nov. 17, 2008, 2 pages.
Written Opinion, issued by the International Bureau in connection with International Application No. PCT/US08/074467, on Nov. 17, 2008, 4 pages.
International Preliminary Report of Patentability, issued by the International Bureau in connection with International Application No. PCT/US10/021535, on Jul. 26, 2011, 1 page.
International Search Report, issued by the International Bureau in connection with International Application No. PCT/US10/021535, on Mar. 23, 2010, 3 pages.
Written Opinion, issued by the International Bureau in connection with International Application No. PCT/US10/021535, on Mar. 23, 2010, 4 pages.
International Preliminary Report of Patentability, issued by the International Bureau in connection with International Application No. PCT/US09/065368, on Jun. 23, 2011, 2 pages.
International Search Report, issued by the International Bureau in connection with International Application No. PCT/US09/065368, on Jan. 21, 2010, 3 pages.
Written Opinion, issued by the International Bureau in connection with International Application No. PCT/US09/065368, on Jan. 21, 2010, 7 pages.
Extended European Search Report, issued by the European Patent Office in connection with European Application No. 08744383.4-2221/2130146, on Jul. 27, 2011, 6 pages.
Extended European Search Report, issued by the European Patent Office in connection with European Application No. 10173095.0-2221, on Dec. 17, 2010, 3 pages.
Extended European Search Report, issued by the European Patent Office in connection with European Application No. 10189294.1-2221, on Mar. 21, 2011, 7 pages.
First Office Action, issued by the State Intellectual Property Office of P.R. China in connection with Patent Application No. 200880104982.1, on Jan. 25, 2011, 15 pages.
First Office Action, issued by the State Intellectual Property Office of P.R. China in connection with Patent Application No. 2008801015007, on May 25, 2011, 8 pages.
First Office Action, issued by the State Intellectual Property Office of P.R. China in connection with Patent Application No. 200880019166.0, on Jul. 22, 2011, 16 pages.
Edgar, et al., "Digital Filters in ERP Research," in Event-Related Potentials: A Methods Handbook pp. 85-113, (Todd C. Handy, ed., 2005), 15 pages.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Friedman, et al., "Event-Related Potential (ERP) Studies of Memory Encoding and Retrieval: A Selective Review," Microscopy Research and Technique 51:6-26, Wiley-Less, Inc. (2000), 23 pages.
Gaillard, "Problems and Paradigms in ERP Research," Biological Psychology, Elsevier Science Publisher B.V. (1988), 10 pages.

Hopf, et al., "Neural Sources of Focused Attention in Visual Search," Cerebral Cortex, 10:1233-1241, Oxford University Press, (Dec. 2000), 9 pages.

Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.

Luck, et al., "The sped of visual attention in schizophrenia: Electrophysiological and behavioral evidence," Schizophrenia Research, pp. 174-195, Elsevier B.V. www.sciencedirect.com, (2006), 22 pages.

Makeig, et al., "Mining event-related brain dynamics," TRENDS in Cognitive Sciences, vol. 8, No. 5, (May 2004), www.sciencedirect.com, 7 pages.

Herrmann, et al., "Mechanisms of human attention: event-related potentials and oscillations," Neuroscience and Biobehavioral Reviews, pp. 465-476, Elsevier Science Ltd., www.elsevier.com/locate/neubiorev, (2001), 12 pages.

Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.

Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.

Paller, et al., "Validating neural correlates of familiarity," TRENDS in Cognitive Sciences, vol. 11, No. 6, www.sciencedirect.com, (May 2, 2007), 8 pages.

Picton, et al., "Guidelines for using human event-related potentials to study cognition: Recording standards and publication criteria," Psychophysiology, pp. 127-152, Society for Psychophysiological Research, (2000), 26 pages.

Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.

Rugg, et al., "Event-related potentials and recognition memory," TRENDS in Cognitive Sciences, vol. 11, No. 6, www.sciencedirect.com, (May 3, 2007), 7 pages.

Rugg, et al., "The ERP and cognitive psychology: conceptual issues," (Sep. 1996), 7 pages.

Kishiyama, et al., "Socioeconomic Disparities Affect Prefrontal Function in Children," Journal of Cognitive Neuroscience pp. 1106-1115, Massachusetts Institute of Technology, (2008), 10 pages.

Spencer, "Averaging, Detection, and Classification of Single-Trial ERPs," in Event-Related Potentials: A Methods Handbook, pp. 209-227, (Todd C. Handy, ed., 2005), 10 pages.

Srinivasan, "High-Resolution EEG: Theory and Practice," in Event-Related Potentials: A Methods Handbook, pp. 167-188, (Todd C. Handy, ed., 2005), 12 pages.

Taheri, et al., "A dry electrode for EEG recording," Electroencephalography and clinical Neurophysiology, pp. 376-383, Elsevier Science Ireland Ltd. (1994), 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

Davidson, et al., "The functional neuroanatomy of emotion and affective style," TRENDS in Cognitive Sciences, vol. 3, No. 1, (Jan. 1999), 11 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.

Rizzolatti et al., "The Mirror-Neuron System," Annu. Rev. Neurosci., vol. 27, pp. 169-192, (Mar. 5, 2004), 30 pages.

Woldorf, "Distortion of ERP averages due to overlap from temporally adjacent ERPs: Analysis and correction," Psychophysiology, Society for Psychophysiological Research, Cambridge University Press (1993), 22 pages.

Woodman, et al., "Serial Deployment of Attention During Visual Search," Journal of Experimental Psychology: Human Perception and Performance, vol. 29, No. 1, pp. 121-138, American Physiological Association (2003), 18 pages.

Filler, "MR Neurography and Diffusion Tensor Imaging: Origins, History & Clinical Impact of the first 50,000 Cases With an Assortment of Efficacy and Utility in a Prospective 5,000 Patent Study Group," Institute for Nerve Medicine, (Nov. 7, 2008), 56 pages.

Yuval-Greenberg, et al., "Transient Induced Gamma-Bands Response in EEG as a Manifestation of Miniature Saccades," Neuron, vol. 58, pp. 429-441, Elsevier Inc. (May 8, 2008), 13 pages.

Knight, et al., "Prefrontal cortex regulates inhibition and excitation in distributed neural networks," Acta Psychologica vol. 101, pp. 159-178, Elsevier (1999), 20 pages.

Gargiulo et al., "A Mobile EEG System With Dry Electrodes," (Nov. 2008), 4 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.

Lui et al., "Marketing Strategies in Virtual Worlds," The Data Base for Advances in Information Systems, vol. 38, No. 4, pp. 77-80, (Nov. 2007), 4 pages.

Cheng, et al. "Gender Differences I the Mu Rhythm of the Human Mirror-Neuron System," PLos ONE, vol. 3, Issue 5, www.plosone.org, (May 2008), 7 pages.

D'Esposito, "From cognitive to neural models of working memory," Phil. Trans. R. Soc. B, doi: 10.1098/rstb.2007.2086, (Mar. 30, 2007), 12 pages.

Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.

Neurofocus—Neuroscientific Analysis for Audience Engagement, accessed on Jan. 8, 2010 at http://web.archive.org/web/20080621114525/www.neurofocus.com/BrandImage.htm, (2008), 2 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Hazlett, et al., "Emotional Response to Television Commercials: Facial EMG vs. Self-Report," Journal of Advertising Research, (Apr. 1999), 17 pages.

Makeig, et al., "Dynamic Brain Sources of Visual Evoked Responses," Science, vol. 295, www.sciencemag.org, (Jan. 25, 2002), 5 pages.

Lewis et al., "Market Researchers make Increasing use of Brain Imaging," ACNR, vol. 5, No. 3, pp. 36-37, (Jul./Aug. 2005), 2 pages.

Haq, "This Is Your Brain on Advertising," BusinessWeek, Market Research, (Oct. 8, 2007), 3 pages.

EEG Protocols, "Protocols for EEG Recording," retrieved from the Internet on Aug. 23, 2011, http://www.q-metrx.com/EEGrecordingProtocols.pdf, (Nov. 13, 2007), 3 pages.

Aaker et al., "Warmth in Advertising: Measurement, Impact, and Sequence Effects," Journal of Consumer Research, vol. 12, No. 4, pp. 365-381, (Mar. 1986), 17 pages.

Belch et al., "Psychophysiological and cognitive Response to Sex in Advertising," Advances in Consumer Research, vol. 9, pp. 424-427, (1982), 6 pages.

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Braeutigam, "Neuroeconomics—From neural systems to economic behavior," Brain Research Bulletin, vol. 67, pp. 355-360, Elsevier, (2005), 6 pages.

Lee et al., "What is 'neuromarketing'? A discussion and agenda for future research," International Journal of Psychophysiology, vol. 63, pp. 199-204, Elsevier (2006), 6 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

Bagozzi et al., "The Role of Emotions in Marketing," Journal of the Academy of Marketing Science, vol. 27, No. 2, pp. 184-206, Academy of Marketing Science (1999), 23 pages.

Blakeslee, "If You Have a 'Buy Button' in Your Brain, What Pushes It?" The New York Times, www.nytimes.com, (Oct. 19, 2004), 3 pages.

Kay et al., "Identifying natural images from human brain activity," Nature, vol. 452, pp. 352-356, Nature Publishing Group, (Mar. 20, 2008), 5 pages.

Nielsen, "Neuroinformatics in Functional Neuroimaging," Informatics and Mathematical Modeling, Technical University of Denmark, (Aug. 30, 2002), 241 pages.

Arousal in Sport, in Encyclopedia of Applied Psychology, vol. 1, p. 159, retrieved from Google Books, (Spielberger, ed., Elsevier Academic Press, 2004), 1 page.

Ziegenfuss, "Neuromarketing: Advertising Ethical & Medical Technology," The Brownstone Journal, vol. XII, Boston University, pp. 69-73, (May 2005), 5 pages.

Zyga, "A Baseball Cap That Can Read Your Mind," PhysOrg.com, located at www.physorg.com/news13015227.html, (May 16, 2008), 11 pages.

Lekakos, "Personalized Advertising Services Through Hybrid Recommendation Methods: The Case of Digital Interactive Television," Department of Informatics, Cyprus University, (2004), 11 pages.

Clifford, "Billboards That Look Back," The New York Times, NYTimes.com, available at http://www.nytimes.com/2008/05/31/business/media/31billboard.html, (May 31, 2008), 4 pages.

U.S. Appl. No. 12/731,868, filed Mar. 25, 2010, (unpublished).
U.S. Appl. No. 13/045,457, filed Mar. 10, 2011, (unpublished).
U.S. Appl. No. 12/778,810, filed May 12, 2010, (unpublished).
U.S. Appl. No. 12/778,828, filed May 12, 2010, (unpublished).
U.S. Appl. No. 13/104,821, filed May 10, 2011, (unpublished).
U.S. Appl. No. 13/104,840, filed May 10, 2011, (unpublished).
U.S. Appl. No. 12/853,197, filed Aug. 9, 2010, (unpublished).
U.S. Appl. No. 12/884,034, filed Sep. 16, 2010, (unpublished).
U.S. Appl. No. 12/868,531, filed Aug. 25, 2010, (unpublished).
U.S. Appl. No. 12/913,102, filed Oct. 27, 2010, (unpublished).
U.S. Appl. No. 12/853,213, filed Aug. 9, 2010, (unpublished).
U.S. Appl. No. 13/105,774, filed May 11, 2011, (unpublished).

Examiner's Answer, issued by the United States Patent and Trademark Office in connection with U.S. Appl. No. 12/234,372, on May 23, 2012, 11 pages.

Advisory Action, issued by the United States Patent and Trademark Office in connection with U.S. Appl. No. 12/234,388, on Aug. 28, 2012, 3 pages.

Examiner's Answer, issued by the United States Patent and Trademark Office in connection with U.S. Appl. No. 12/410,380, on Jun. 8, 2012, 12 pages.

Examiner's Answer, issued by the United States Patent and Trademark Office in connection with U.S. Appl. No. 12/410,372, on Aug. 3, 2012, 8 pages.

Office Action, issued by the United States Patent and Trademark Office in connection with U.S. Appl. No. 12/545,455, on Aug. 29, 2012, 11 pages.

Office Action, issued by the United States Patent and Trademark Office in connection with U.S. Appl. No. 12/778,810, on Aug. 31, 2012, 12 pages.

Office Action, issued by the United States Patent and Trademark Office in connection with U.S. Appl. No. 12/778,828, on Aug. 30, 2012, 9 pages.

Oberman et al., "EEG evidence for mirror neuron activity during the observation of human and robot actionsAug. 29, 2012 Toward an analysis of the human qualities of interactive robots," Neurocomputing 70 (2007) 2194-2203, 10 pages.

Office Action, issued by the United States Patent and Trademark Office in connection with U.S. Appl. No. 12/135,066, on Sep. 29, 2011, 37 pages.

Restriction Requirement, issued by the United States Patent and Trademark Office in connection with U.S. Appl. No. 12/056,225, on Oct. 3, 2011, 6 pages.

Office Action, issued by the United States Patent and Trademark Office in connection with U.S. Appl. No. 12/234,388, on Oct. 12, 2011, 27 pages.

Office Action, issued by the United States Patent and Trademark Office in connection with U.S. Appl. No. 12/234,372, on Oct. 13, 2011, 22 pages.

Office Action, issued by the United States Patent and Trademark Office in connection with U.S. Appl. No. 12/410,380, on Oct. 19, 2011, 21 pages.

Office Action, issued by the United States Patent and Trademark Office in connection with U.S. Appl. No. 12/357,315, on Oct. 26, 2011, 41 pages.

Office Action, issued by the United States Patent and Trademark Office in connection with U.S. Appl. No. 12/122,240, on Oct. 27, 2011, 39 pages.

Final Rejection, issued by the United States Patent and Trademark Office in connection with U.S. Appl. No. 12/056,221, on Nov. 28, 2011, 44 pages.

Office Action, issued by the United States Patent and Trademark Office in connection with U.S. Appl. No. 12/608,660, on Dec. 7, 2011, 8 pages.

Office Action, issued by the United States Patent and Trademark Office in connection with U.S. Appl. No. 12/113,863, on Dec. 22, 2011, 17 pages.

Office Action, issued by the United States Patent and Trademark Office in connection with U.S. Appl. No. 12/122,262, on Dec. 22, 2011, 17 pages.

Office Action, issued by the United States Patent and Trademark Office in connection with U.S. Appl. No. 12/135,074, on Dec. 22, 2011, 16 pages.

Office Action, issued by the United States Patent and Trademark Office in connection with U.S. Appl. No. 12/199,557, on Dec. 22, 2011, 17 pages.

Office Action, issued by the United States Patent and Trademark Office in connection with U.S. Appl. No. 12/199,596, on Dec. 22, 2011, 15 pages.

Office Action, issued by the United States Patent and Trademark Office in connection with U.S. Appl. No. 12/200,813, on Dec. 22, 2011, 18 pages.

Office Action, issued by the United States Patent and Trademark Office in connection with U.S. Appl. No. 12/199,583, on Dec. 29, 2011, 18 pages.

Final Rejection, issued by the United States Patent and Trademark Office in connection with U.S. Appl. No. 12/410,372, on Jan. 3, 2012, 10 pages.

Final Rejection, issued by the United States Patent and Trademark Office in connection with U.S. Appl. No. 12/413,297, on Jan. 4, 2012, 10 pages.

Office Action, issued by the United States Patent and Trademark Office in connection with U.S. Appl. No. 12/544,921, on Jan. 9, 2012, 13 pages.

Office Action, issued by the United States Patent and Trademark Office in connection with U.S. Appl. No. 12/357,302, on Jan. 17, 2012, 11 pages.

Office Action, issued by the United States Patent and Trademark Office in connection with U.S. Appl. No. 12/056,225, on Jan. 20, 2012, 12 pages.

Final Rejection, issued by the United States Patent and Trademark Office in connection with U.S. Appl. No. 12/135,066, on Jan. 24, 2012, 12 pages.

Office Action, issued by the United States Patent and Trademark Office in connection with U.S. Appl. No. 12/546,586, on Feb. 1, 2012, 17 pages.

Decision of Rejection, issued by the State Intellectual Property Office of P.R. China in connection with Patent Application No. 200880104982.1, on Sep. 23, 2011, 10 pages.

Extended European Search Report, issued by the European Patent Office in connection with European Application No. 11006934.1-2221, on Oct. 25, 2011, 5 pages.

First Office Action, issued by the State Intellectual Property Office of P.R. China in connection with Patent Application No. 200880017883.X, on Nov. 30, 2011, 16 pages.

Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.

Meriam-Webster Online Dictionary definition for "tangible," available at http://www.meriam-webster.com/dictionary/tangible, 1 page.

Restriction Requirement, issued by the United States Patent and Trademark Office in connection with U.S. Appl. No. 12/544,958, on Feb. 10, 2012, 6 pages.

Final Rejection, issued by the United States Patent and Trademark Office in connection with U.S. Appl. No. 12/135,069, on Feb. 14, 2012, 36 pages.

Final Rejection, issued by the United States Patent and Trademark Office in connection with U.S. Appl. No. 12/608,685, on Jul. 30, 2012, 15 pages.

Office Action, issued by the United States Patent and Trademark Office in connection with U.S. Appl. No. 12/056,211, on Feb. 16, 2012, 16 pages.

Final Rejection, issued by the United States Patent and Trademark Office in connection with U.S. Appl. No. 12/056,190, on Feb. 17, 2012, 22 pages.

Mosby's Dictionary of Medicine, Nursing, & Health Professions, 2009, Mosby, Inc., Definition of Alpha Wave, 1 page.

Mosby's Dictionary of Medicine, Nursing, & Health Professions, 2009, Mosby, Inc., Definition of Beta Wave, 1 page.

Office Action, issued by the United States Patent and Trademark Office in connection with U.S. Appl. No. 12/122,253, on Feb. 17, 2012, 20 pages.

Office Action, issued by the United States Patent and Trademark Office in connection with U.S. Appl. No. 12/182,874, on Feb. 17, 2012, 15 pages.

Meriam Webster Online Dictionary, Definition of Virtual Reality, available at http://www.meriam-webster.com/dictionary/virtual%20reality, 2 page.

Office Action, issued by the United States Patent and Trademark Office in connection with U.S. Appl. No. 12/868,531, on Mar. 1, 2012, 7 pages.

English Translation of Office Action, issued by the Israel Patent Office in connection with Patent Application No. 203176, on Feb. 21, 2012, 2 pages.

English Translation of Office Action, issued by the Israel Patent Office in connection with Patent Application No. 203177, on Mar. 1, 2012, 2 pages.

Office Action, issued by the United States Patent and Trademark Office in connection with U.S. Appl. No. 12/182,851, on Mar. 14, 2012, 17 pages.

Office Action, issued by the United States Patent and Trademark Office in connection with U.S. Appl. No. 12/846,242, on Mar. 29, 2012, 16 pages.

Office Action, issued by the United States Patent and Trademark Office in connection with U.S. Appl. No. 12/608,685, on Mar. 29, 2012, 17 pages.

Second Office Action, issued by the State Intellectual Property Office of P.R. China in connection with Patent Application No. 200880101500.7, on Apr. 5, 2012, 5 pages.

Office Action, issued by the United States Patent and Trademark Office in connection with U.S. Appl. No. 12/234,388, on Apr. 6, 2012, 6 pages.

Office Action, issued by the United States Patent and Trademark Office in connection with U.S. Appl. No. 12/357,3158, on Apr. 9, 2012, 17 pages.

Office Action, issued by the United States Patent and Trademark Office in connection with U.S. Appl. No. 12/544,958, on May 2, 2012, 15 pages.

Newell et al., "Categorical perception of familiar objects," Cognition, vol. 85, Issue 2, pp. 113-143 (Sep. 2002), 31 pages.

Bimler et al., "Categorical perception of facial expressions of emotion: Evidence from multidimensional scaling," Cognition and Emotion, vol. 15(5), pp. 633-658 (Sep. 2001), 26 pages.

de Gelder et al., "Categorical Perception of Facial Expressions: Categories and their Internal Structure," Cognition and Emotion, vol. 11(1), pp. 1-23 (1997), 23 pages.

Griss et al., "Characterization of micromachined spiked biopotential electrodes", Biomedical Engineering, IEEE Transactions (Jun. 2002), 8 pages.

Sullivan et al., "A brain-machine interface using dry-contact, low-noise EEG sensors," In Proceedings of the 2008 IEEE International Symposium on Circuits and Systems, (May 18, 2008), 4 pages.

"User monitoring," Sapien Systems, available at http://web.archive.org/web/20030818043339/http:/www.sapiensystems.com/eyetracking.html, (Aug. 18, 2003), 1 page.

Padgett et al., "Categorical Perception in Facial Emotion Classification," In Proceedings of the 18th Annual Conference of the Cognitive Science Society, pp. 249-253 (1996), 5 pages.

Office Action, issued by the United States Patent and Trademark Office in connection with U.S. Appl. No. 12/056,225, on Jun. 15, 2012, 9 pages.

Office Action, issued by the United States Patent and Trademark Office in connection with U.S. Appl. No. 12/135,066, on Jun. 21, 2012, 10 pages.

Second Office Action, issued by the State Intellectual Property Office of P.R. China in connection with Patent Application No. 200880019166.0, on Jun. 5, 2012, 8 pages.

Second Office Action, issued by the State Intellectual Property Office of P.R. China in connection with Patent Application No. 200880104982.1, on Jun. 29, 2012, 5 pages.

Notice of Allowance, issued by the United States Patent and Trademark Office in connection with U.S. Appl. No. 12/357,302, on May 7, 2012, 11 pages.

Office Action, issued by the United States Patent and Trademark Office in connection with U.S. Appl. No. 12/544,934, on Jun. 18, 2012, 11 pages.

Restriction Requirement, issued by the United States Patent and Trademark Office in connection with U.S. Appl. No. 12/545,455, on Jun. 13, 2012, 5 pages.

Final Rejection, issued by the United States Patent and Trademark Office in connection with U.S. Appl. No. 12/608,660, on Jul. 10, 2012, 14 pages.

Notice of Allowance, issued by the United States Patent and Trademark Office in connection with U.S. Appl. No. 12/608,696, on May 15, 2012, 6 pages.

Notice of Allowance, issued by the United States Patent and Trademark Office in connection with U.S. Appl. No. 12/868,531, on May 8, 2012, 11 pages.

Krugman, "Brain Wave Measures of Media Involvement," Journal of Advertising Research vol. 11, 3-9 (Feb. 1971), 7 pages.

Jung et al., "Analysis and Visualization of Single-Trial Event-Related Potentials," Human Brain Mapping vol. 14, 166-185 (2001), 20 pages.

The Mathworks, Inc., "MATLAB Data Analysis: Version 7," p. 4-19 (2005), 3 pages.

Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.

Krakow et al., "Methodology: EEG-correlated fMRI," Functional Imaging in the Epilepsies, (Lippincott Williams & Wilkins, 2000), 17 pages.

Allen et al., "A Method of Removing Imaging Artifact from Continuous EEG Recorded during Functional MRI," Neuroimage, vol. 12, 230-239, (Aug. 2000), 12 pages.

Klimesch, "EEG alpha and theta oscillations reflect cognitive and memory performance a review and analysis," Brain Research Reviews, vol. 29, 169-195, (1999), 27 pages.

Office Action, issued by the United States Patent and Trademark Office in connection with U.S. Appl. No. 12/357,315, on Oct. 9, 2012, 33 pages.

* cited by examiner

METHODS AND APPARATUS FOR PROVIDING PERSONALIZED MEDIA IN VIDEO

TECHNICAL FIELD

The present disclosure relates to personalizing media in video.

DESCRIPTION OF RELATED ART

A variety of conventional systems are available for delivering and manipulating video. In some instances, personal video recorders or digital video recorders store video and audio to allow user playback and/or manipulation of the video. A user may fast forward, rewind, skip forward, and/or play video back at varying speeds. In other instances, video discs may hold video for playback and/or manipulation on video disc players. Video disc players may similarly allow a user to fast forward, rewind, skip forward, and/or play video back at varying speeds. Computing systems may also hold video in memory that allows playback and manipulation of the video.

Although a variety of video delivery and manipulation mechanisms are available, the ability to personalize media is limited. Consequently, it is desirable to provide improved methods and apparatus for embedding personalized media in video.

BRIEF DESCRIPTION OF THE DRAWINGS

The disclosure may best be understood by reference to the following description taken in conjunction with the accompanying drawings, which illustrate particular example embodiments.

DESCRIPTION OF PARTICULAR EMBODIMENTS

Figure 1:
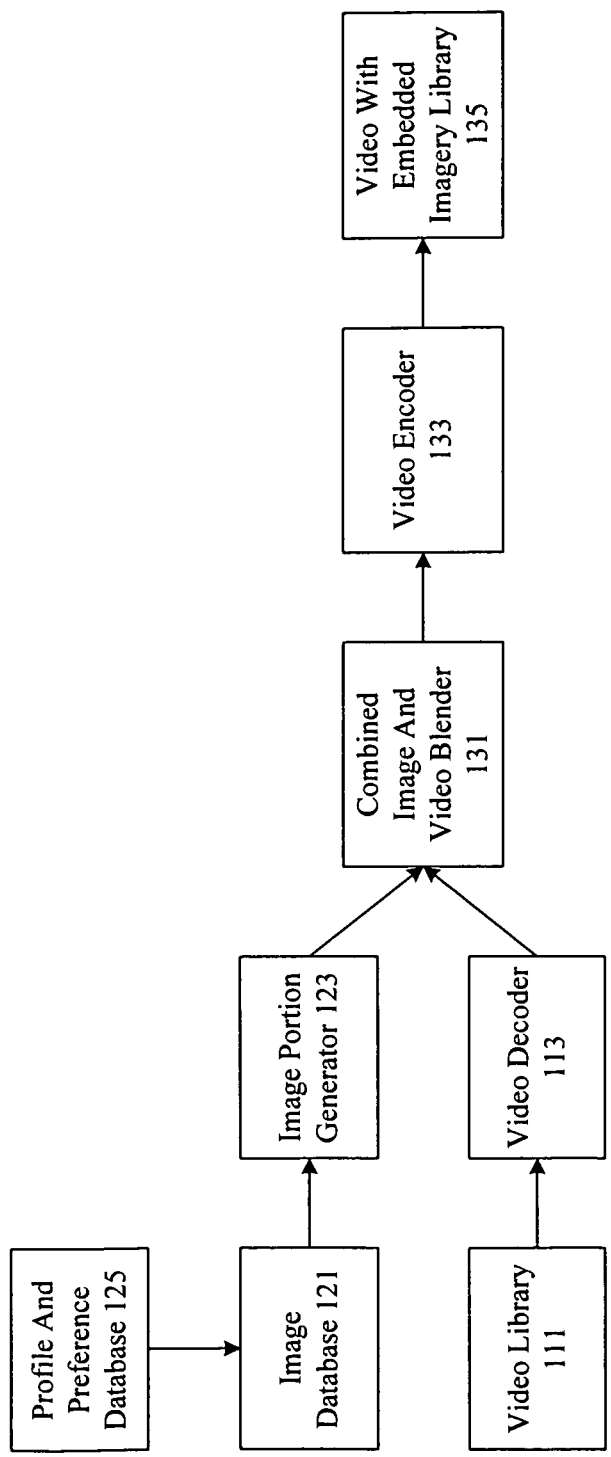
FIG. 1 illustrates one example of a system for providing personalized imagery.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques and mechanisms of the present invention will be described in the context of particular types of media. However, it should be noted that the techniques and mechanisms of the present invention apply to a variety of different types of media. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

A system provides personalized media in video for presentation using a video decoder in a device such as a video recorder, hardware or software player, computer system, or television. The personalized media may be embedded or hidden in a video stream or provided in a separate stream. A video decoder determines profile and preference information associated with a viewer, group, or demographic and personalizes commercial content using the profile and preference information. The system includes personalized media by introducing, embedding, overlaying, etc., media on video during commercial breaks. Personalized media may be provided during normal viewing or may be provided when a skip forward or fast forward request is received. The system may also evaluate personalization mechanisms using neuro-response measurements.

Example Embodiments

Conventional mechanisms for personalizing media such as advertisements are limited. Some video web servers maintain information about user preferences or past viewing profiles and select particular videos as recommended offerings. In other examples, web servers select particular advertisements for a viewer. However, these may have limited effectiveness and the advertisements may not be noticed at all if a viewer is focused on the video itself. Some systems modify the video itself. A frame of video may be replaced in its entirety with a different substitute frame. The single frame may be processed subconsciously by a viewer. However, replaced frames are generally not looked upon positively. In other systems, video includes watermarking or faint imagery. However, this imagery may only be discernible upon close examination. Personalization using these mechanisms is also limited or non-existent.

Viewers will often fast forward or rewind video data or playback video data at accelerated rates. Viewers will also often use these mechanisms to skip commercials or portions of content that they do not want to see. As commercial skipping becomes more prevalent, the techniques of the present invention recognize that it is useful to provide advertisers, content providers, and service providers with a mechanism for introducing additional discernible content to viewers. Personalized content would be particularly effective. According to various embodiments, media such as imagery can be introduced with or without any hardware or player modifications. This allows image embedding with minimal investment, as no new equipment is required. In other embodiments, media is introduced with hardware or player modifications. Additional discernible content becomes more effective and valuable to advertisers as content becomes more personalized. In some instances, personalized media is introduced and presented to a viewer when commercial skipping occurs, although personalized media can be introduced at any time. Media may be personalized based on user, group, and demographic information.

According to various embodiments, personalized media may be embedded or hidden in a video stream, or may be provided in a separate stream entirely. Personalized media may be placed on a video as an overlay and embedded in the video itself. According to various embodiments, video frames are modified to include different portions of a personalized image, message, or video. In particular embodiments, the different portions may be different subsets of image pixels. The different image portions may be blended with surrounding imagery to somewhat match hue, saturation, value and/or other image qualities. When the video is viewed at normal or near normal speeds, the portions of the image and the personalized image are not easily discernible. However, when the personalized image is played back at an accelerated speed in either the forward or reverse direction, the different portions of the personalized image coalesce to form a discernible image.

In one example, different segments of a line are embedded onto consecutive frames of video. When the frames are played back at 4×, 8×, or 60× speed, the segments combine to create a discernible line. In another example, a subset of pixels of a company logo are embedded in the frames of an advertisement. According to various embodiments, when the video is played at normal speeds, the logo is not discernible. However, when the video is played at accelerated speeds, the different subsets of pixels in the different frames combine to form a discernible company logo. In some examples, the name of a viewer along with a company logo is shown when a user fast forwards through a commercial. In still other examples, the alternate media may meet a discernibility threshold whether the playback occurs at normal or accelerated rates.

In some examples, the personalized imagery may include text providing location information or a summary about a portion of show being fast forwarded. Instead of watching a 10 minute scene, a viewer may read a summary of the scene or see a title of the scene while fast forwarding through the 10 minute scene at 8× speed. The summary or title would not be discernible when the scene is played at normal speed.

FIG. 1 illustrates one example of a system for embedding personalized media such as imagery in a video. Although a particular embodiment for embedding a personalized image is described, it should be noted that personalized video, text, audio, imagery, and data can be embedded or provided as an overlay. According to various embodiments, the video may be streaming, file-based, analog, digital, real-time, time-delayed, etc. In particular embodiments, a video library 111 provides video to a video decoder 113. In some instances, video may not require decoding. In other examples, video may need to be decompressed and expressed as sequential frames. A profile and preference database 125 is connected to a media database such as an image database 121. Profile and/or preference information is referred to herein as personalization information. Examples of profile information include age, gender, income, race, employment status, etc. Examples of preference information include interests, purchasing history, viewing characteristics, etc. According to various embodiments, a profile and preference database 125 maintains information about viewers.

In particular embodiments, the viewers manually enter profile and preference information. In other examples, the profile and preference database 125 is automatically compiled or dynamically compiled by a video recorder, content provider, service providers, etc. The profile and preference database 125 allows selection and customization of media including video, logos, text, and images for presentation to particular users. According to various embodiments, the profile and preference database 125 allows generation of an image with the viewer's name. In other examples, the profile and preference database 125 allows selection of images that suit particular viewer interests. Profile and preference database 125 may also include information about group and demographic preferences.

An image database 121 uses information from the profile and preference database 125 to select and/or generate images for presentation to a viewer. The image database 121 provides images including text, data, logos, pictures, and even dynamic and changing imagery to an image portion generator 123. The image portion generator 123 selects portions of the imagery for inclusion in video frames. According to various embodiments, the image portion generator 123 randomly selects subsets of pixels of the image for inclusion in sequential frames. In particular embodiments, the image portion generator 123 intelligently selects subsets of pixels of the image for inclusion in sequential frames.

In some examples, the image portion generator 123 may be connected to a video decoder 113 to obtain information about the video itself. The image portions and video frames are passed to a combined image and video blender 131. The combined image and video blender 131 melds the image portions onto the video According to various embodiments, boundaries and colors between the image portions and video are blended. The combined image and video blender may also identify particular locations in frames for embedding the image. According to various embodiments, images are embedded in portions of video that are relatively static and uniform, such as a part of a video frame showing a blue sky or a blank wall.

Image portions may be made more transparent or blurred before embedding them on the video to make the image portions less visible during regular playback. In other examples, images may be outlined more clearly, made more opaque, or generated with higher contrast colors before embedding them on video to make the images more discernible during accelerated playback. According to various embodiments, survey based and/or neuro-response analysis is used to determine the optimal combination or clarity, opacity, and contrast. In other examples, neuro-response analysis is used to determine the optimal combination of hue, saturation, and value for various pixels in the image and image portions.

Video frames embedded with image portions are then passed to video encoder 133. In some examples, no video encoding is required. The video with embedded imagery is then stored in a video with embedded imagery library 135. In particular embodiments, the video is presented in real-time to consumers without use of any storage mechanism.

Figure 2B:
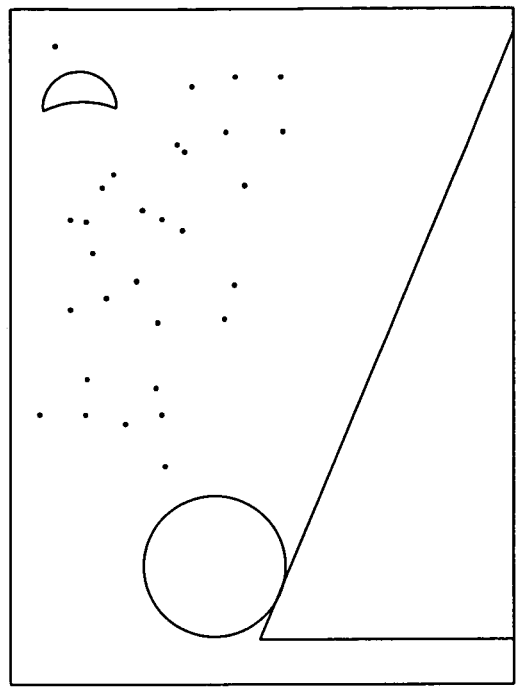
FIGS. 2A-K illustrate examples of different portions of an personalized image and video.
Figure 2A:
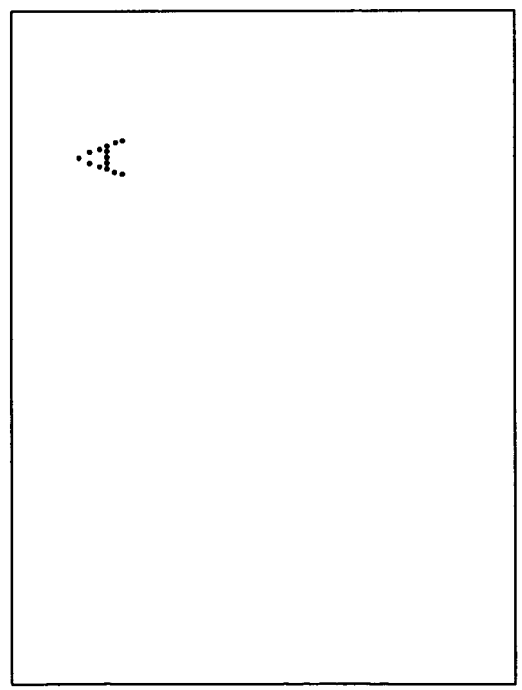
Figure 2E:
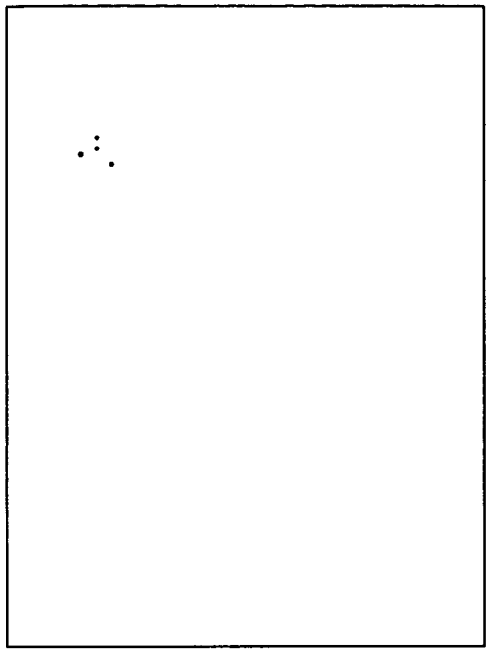
Figure 2F:
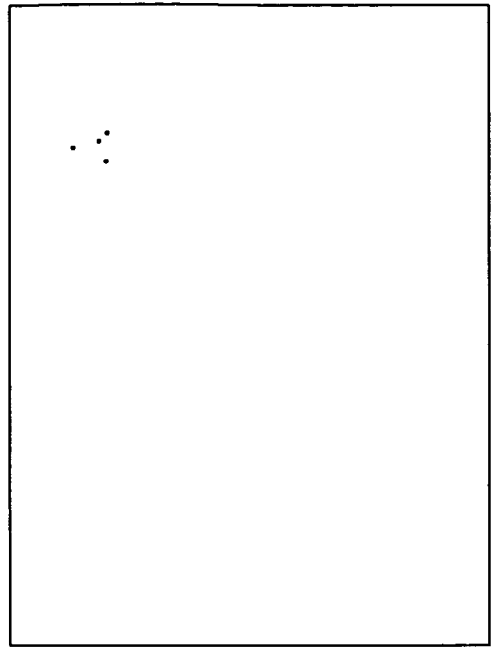
Figure 2C:
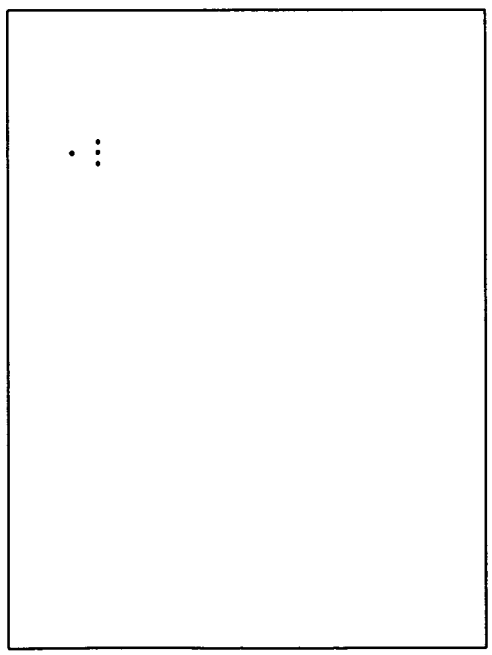
Figure 2D:
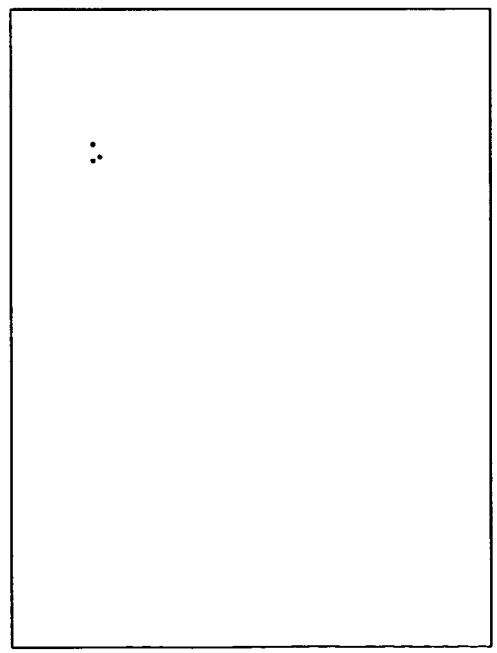
Figure 2G:
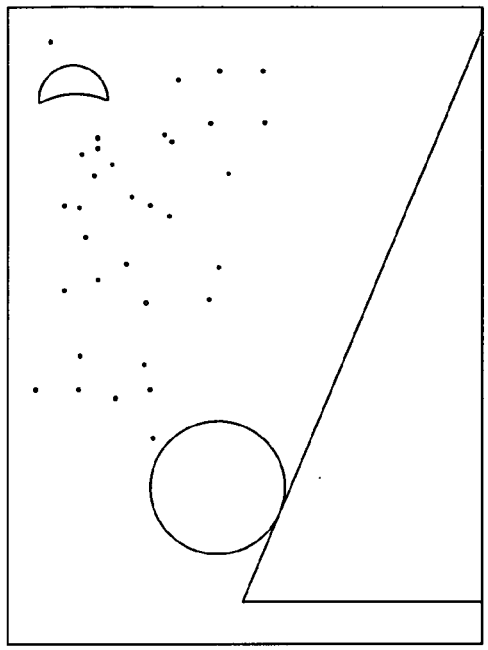
Figure 2I:
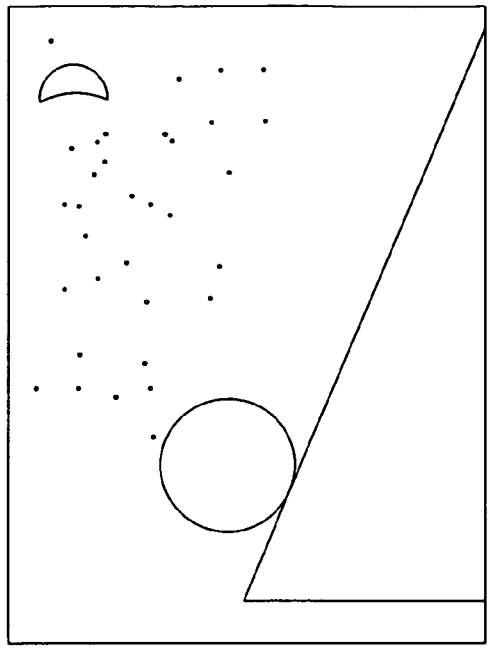
Figure 2H:
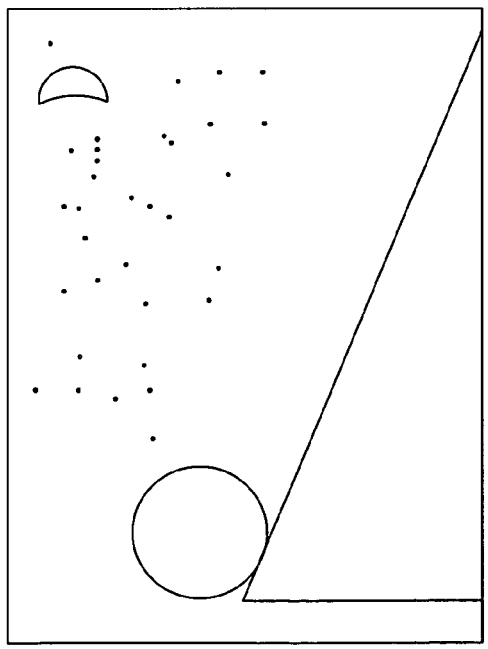
Figure 2J:
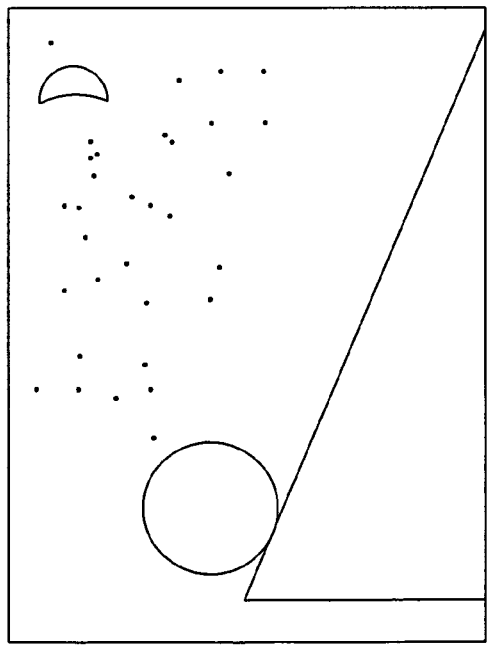
Figure 2K:
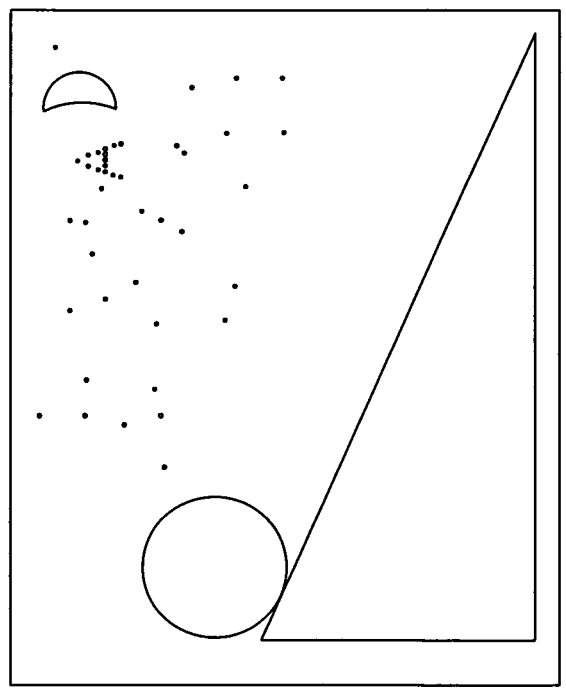

FIG. 2A illustrates one example of an image that can be embedded onto video. According to various embodiments, the image is the name of a viewer. However, for purposes of illustration, the image of a letter "A" in pixel form is shown. FIG. 2B shows one frame of a video of a ball rolling down a ramp against a night time sky. FIGS. 2C-2F illustrate portions of an image of the letter "A". According to various embodiments, a subset of pixels of the image are selected for embedding on each frame. When the frames are viewed at normal speed, no image is discernible. However, when the frames are played at accelerated speeds, the pixels coalesce to form an image. FIGS. 2G-2J show video frames with embedded image portions. FIGS. 2G-2J include embedded images in FIGS. 2C-2F respectively. FIG. 2K shows a full image of the letter "A" embedded on a frame in 2K. According to various embodiments, the full image of the letter "A" is what is discernible when the frames are played at an accelerated rate.

Figure 3:
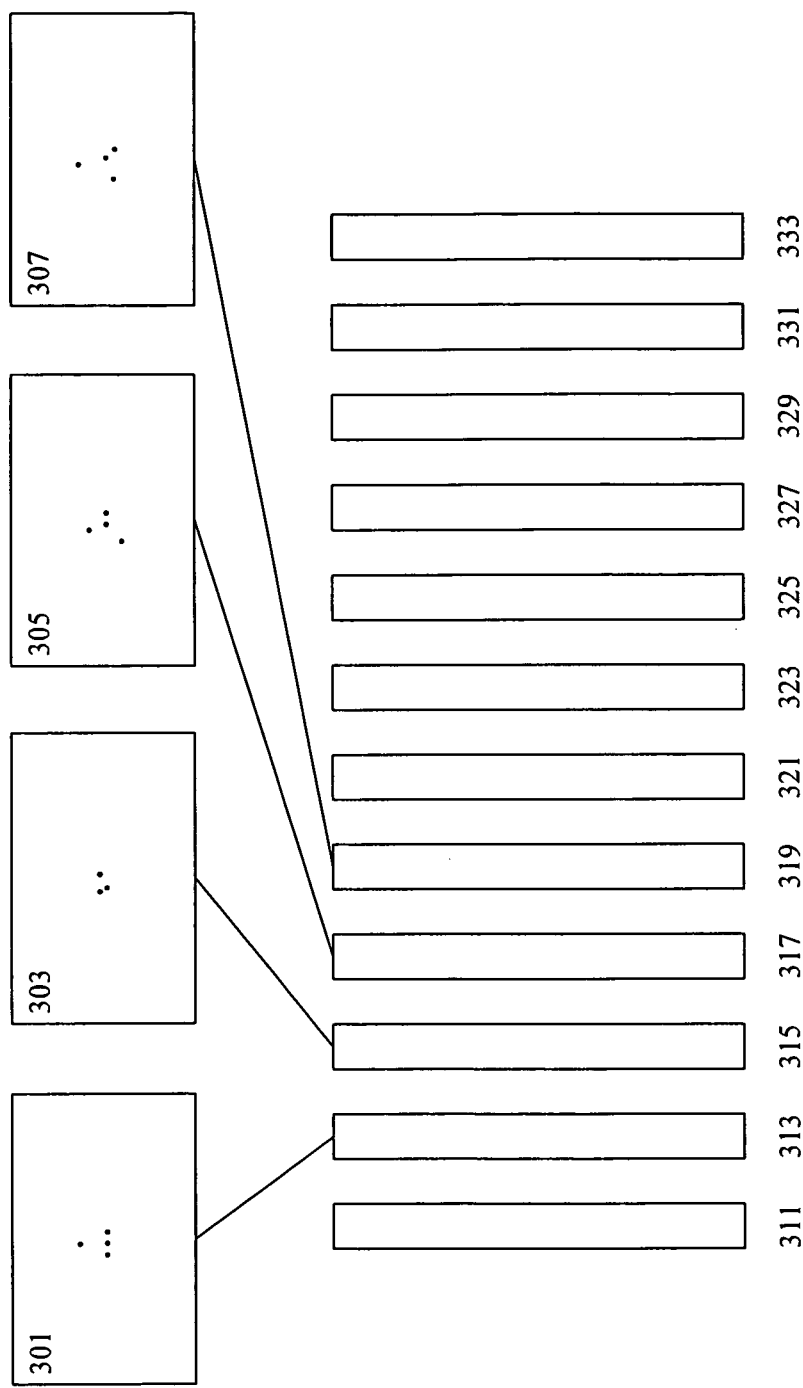
FIG. 3 illustrates one example of a series of video frames.

FIG. 3 illustrates one example of a sequence of frames. Video includes frames 311, 313, 315, 317, 319, 321, 323, 325, 327, 329, 331, and 333. Personalized image portions 301, 303, 305, and 307 are provided for inclusion in video frames. According to various embodiments, image portion 301 is included in frame 313, image portion 303 is included in frame 315, image portion 305 is included in frame 317, and image portion 307 is included in frame 319. In particular embodiments, image portions are included in sequential frames. However, in many instances, not every frame needs to have embedded image portions. In some examples, multiple frames in a sequence include the same image portion.

Figure 4:
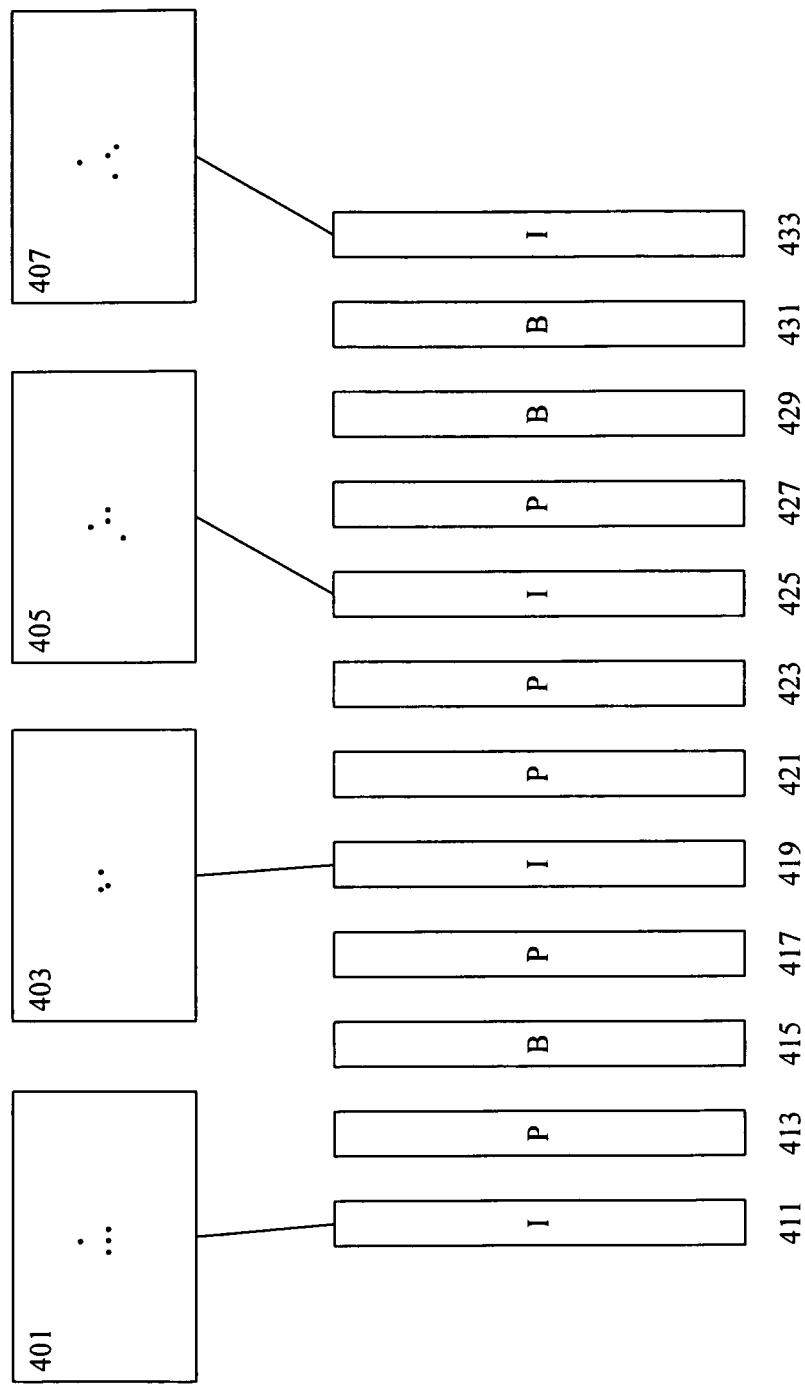
FIG. 4 illustrates another example of a series of video frames.

FIG. 4 illustrates another example of a sequence of frames. Many video encoding mechanisms include different types of frames. According to various embodiments, frames include intra-coded frames (I-frames), predicted frames (P-frames), and bi-predictive frames (B-frames). I-frames provide substantially all of the data needed to present a full picture. On the other hand, P-frames and B-frames provide information about differences between the predictive frame and an I-frame. Predictive frames such as B-frames and P-frames are smaller and more bandwidth efficient than I-frames. According to various embodiments, the techniques of the present invention modify only I-frames. In particular embodiments, only I-frames are embedded with image portions.

According to various embodiments, frames sequences 411, 413, 415, 417, 419, 421, 423, 425, 427, 429, 431, and 433 include I-frames 411, 419, 425, and 433. The frame sequence also includes predictive frames including P-frames 413, 417, 421, 423, and 427 as well as B-frames 415, 429, and 431. In particular embodiments, image portions are embedded on I-frames. Pixel subsets are shown as examples of portions of an image A. Image portion 401 is blended with I-frame 411, image portion 403 is blended with I-frame 419, image portion 405 is blended with I-frame 425, and image portion 407 is blended with I-frame 433.

A variety of survey based and neuro-response based mechanisms can be used to determine the effectiveness of embedding images into video. Using feedback from survey based and/or neuro-response based mechanisms can allow adjustment of the type of image, the saliency of the image in the video, the location of the image, duration and size of the image, and dynamism of the image. For example, survey based and/or neuro-response mechanisms may determine that an image is hardly noticed by a majority of viewers even when the video is played at a variety of accelerated speeds. In particular embodiments, the image contrast and size may be increased. In other examples, survey based and/or neuro-response mechanisms may indicate that images are noticeable and distracting even during playback at regular speeds. Additional blending mechanisms may be applied to an image to reduce the noticeability of an image during regular playback. The position or size of the image may also be adjusted.

Figure 5:
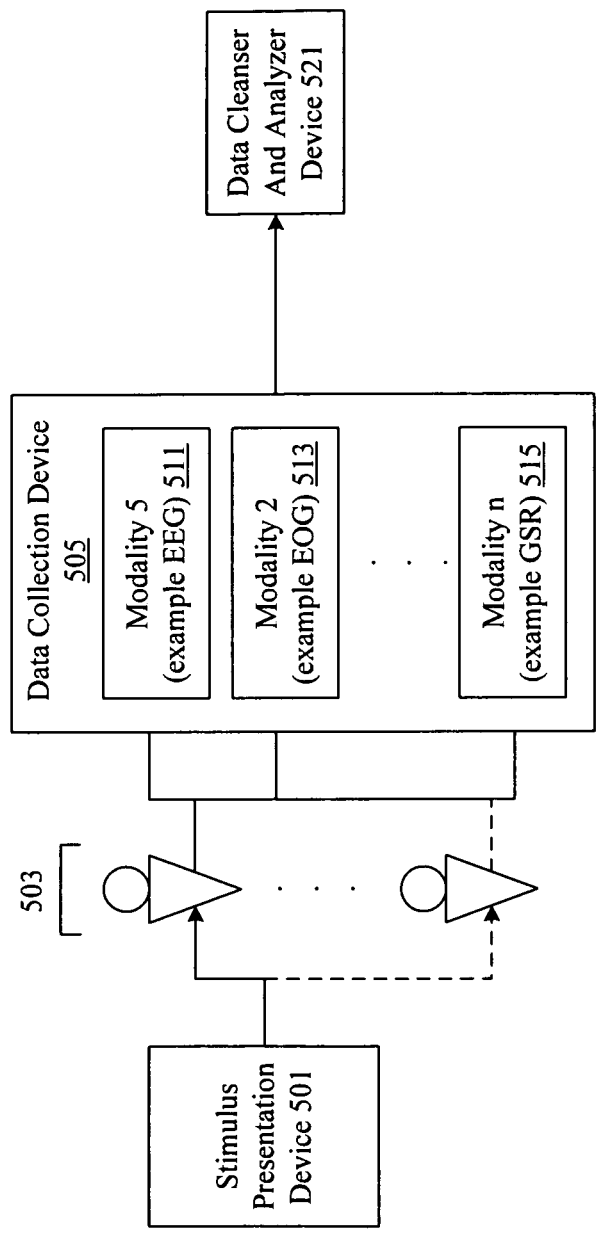
FIG. 5 illustrates one example of a system for analyzing video personalized imagery.

FIG. 5 illustrates one example of a system for selecting and evaluating personalized imagery for video by using central nervous system, autonomic nervous system, and/or effector measures. According to various embodiments, the video embedded media system includes a stimulus presentation device 501. In particular embodiments, the stimulus presentation device 501 is merely a display, monitor, screen, etc., that displays stimulus material to a user. The stimulus material may be videos with embedded images or the images themselves. Continuous and discrete modes are supported. According to various embodiments, the stimulus presentation device 501 also has protocol generation capability to allow intelligent customization of stimuli provided to multiple subjects in different markets.

According to various embodiments, stimulus presentation device 501 could include devices such as televisions, cable consoles, computers and monitors, projection systems, display devices, speakers, tactile surfaces, etc., for presenting the video from different networks, local networks, cable channels, syndicated sources, websites, internet content aggregators, portals, service providers, etc.

According to various embodiments, the subjects 503 are connected to data collection devices 505. The data collection devices 505 may include a variety of neuro-response measurement mechanisms including neurological and neurophysiological measurements systems. According to various embodiments, neuro-response data includes central nervous system, autonomic nervous system, and effector data.

Some examples of central nervous system measurement mechanisms include Functional Magnetic Resonance Imaging (fMRI) and Electroencephalography (EEG). fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

According to various embodiments, the techniques and mechanisms of the present invention intelligently blend multiple modes and manifestations of precognitive neural signatures with cognitive neural signatures and post cognitive neurophysiological manifestations to more accurately allow assessment of embedded imagery in video. In some examples, autonomic nervous system measures are themselves used to validate central nervous system measures. Effector and behavior responses are blended and combined with other measures. According to various embodiments, central nervous system, autonomic nervous system, and effector system measurements are aggregated into a measurement that allows definitive evaluation stimulus material In particular embodiments, the data collection devices 505 include EEG 511, EOG 513, and GSR 515. In some instances, only a single data collection device is used. Data collection may proceed with or without human supervision.

The data collection device 505 collects neuro-response data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular embodiments, data collected is digitally sampled and stored for later analysis. In particular embodiments, the data collected could be analyzed in real-time. According to particular embodiments, the digital sampling rates are adaptively chosen based on the neuro-physiological and neurological data being measured.

In one particular embodiment, the video embedded imagery system includes EEG 511 measurements made using scalp level electrodes, EOG 513 measurements made using shielded electrodes to track eye data, GSR 515 measurements performed using a differential measurement system, a facial muscular measurement through shielded electrodes placed at specific locations on the face, and a facial affect graphic and video analyzer adaptively derived for each individual.

In particular embodiments, the data collection devices are clock synchronized with a stimulus presentation device 501. In particular embodiments, the data collection devices 505 also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions. According to various embodiments, the data collection devices include mechanisms for not only monitoring subject neuro-response to stimulus materials, but also include mechanisms for identifying and monitoring the stimulus materials. For example, data collection devices 505 may be synchronized with a set-top box to monitor channel changes. In other examples, data collection devices 505 may be directionally synchronized to monitor when a subject is no longer paying attention to stimulus material. In still other examples, the data collection devices 505 may receive and store stimulus material generally being viewed by the subject, whether the stimulus is a program, a commercial, printed material, or a scene outside a window. The data collected allows analysis of neuro-response information and correlation of the information to actual stimulus material and not mere subject distractions.

According to various embodiments, the video embedded imagery system also includes a data cleanser and analyzer device 521. In particular embodiments, the data cleanser and analyzer device 521 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject, e.g. a phone ringing while a subject is viewing a video) and endogenous artifacts (where the source could be neurophysiological, e.g. muscle movements, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various embodiments, the data cleanser and analyzer device 521 is implemented using hardware, firmware, and/or software.

The data analyzer portion uses a variety of mechanisms to analyze underlying data in the system to determine resonance. According to various embodiments, the data analyzer customizes and extracts the independent neurological and neuro-physiological parameters for each individual in each modality, and blends the estimates within a modality as well as across modalities to elicit an enhanced response to the presented stimulus material. In particular embodiments, the data analyzer aggregates the response measures across subjects in a dataset.

According to various embodiments, neurological and neuro-physiological signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, distribution, as well as fuzzy estimates of attention, emotional engagement and memory retention responses.

According to various embodiments, the data analyzer may include an intra-modality response synthesizer and a cross-modality response synthesizer. In particular embodiments, the intra-modality response synthesizer is configured to customize and extract the independent neurological and neuro-physiological parameters for each individual in each modality and blend the estimates within a modality analytically to elicit an enhanced response to the presented stimuli. In particular embodiments, the intra-modality response synthesizer also aggregates data from different subjects in a dataset.

According to various embodiments, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various embodiments, the data analyzer also includes a composite enhanced effectiveness estimator (CEEE) that combines the enhanced responses and estimates from each modality to provide a blended estimate of the effectiveness. In particular embodiments, blended estimates are provided for each exposure of a subject to stimulus materials. The blended estimates are evaluated over time to assess resonance characteristics. According to various embodiments, numerical values are assigned to each blended estimate. The numerical values may correspond to the intensity of neuro-response measurements, the significance of peaks, the change between peaks, etc. Higher numerical values may correspond to higher significance in neuro-response intensity. Lower numerical values may correspond to lower significance or even insignificant neuro-response activity. In other examples, multiple values are assigned to each blended estimate. In still other examples, blended estimates of neuro-response significance are graphically represented to show changes after repeated exposure.

According to various embodiments, a data analyzer passes data to a resonance estimator that assesses and extracts resonance patterns. In particular embodiments, the resonance estimator determines entity positions in various stimulus segments and matches position information with eye tracking paths while correlating saccades with neural assessments of attention, memory retention, and emotional engagement. In particular embodiments, the resonance estimator stores data in the priming repository system. As with a variety of the components in the system, various repositories can be colocated with the rest of the system and the user, or could be implemented in remote locations.

Figure 6:
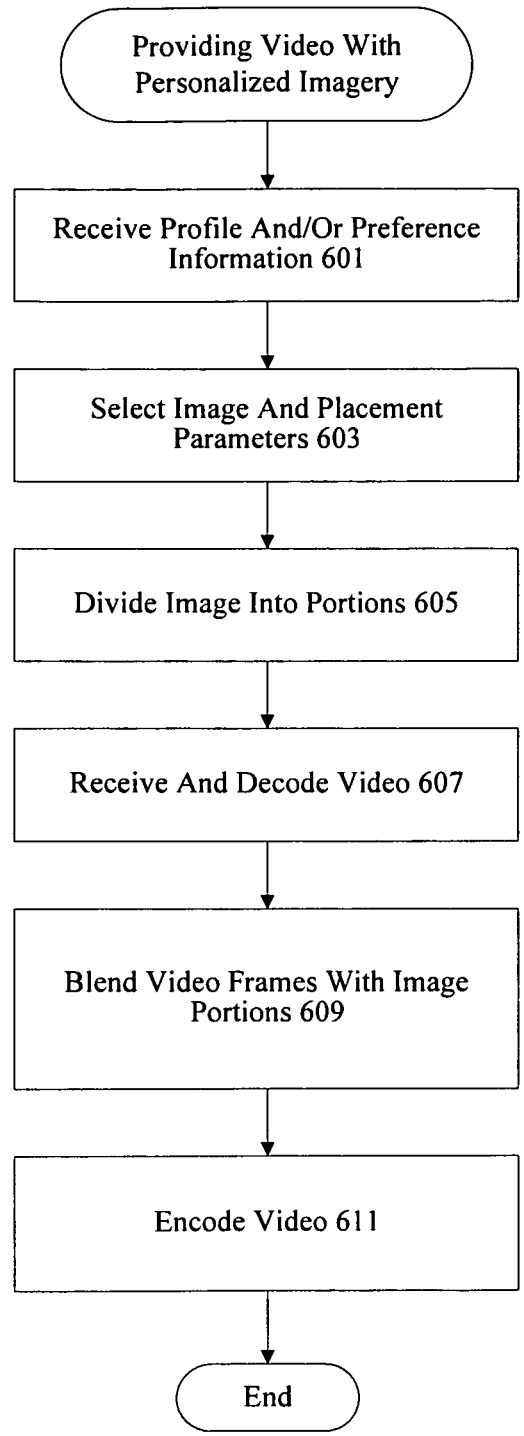
FIG. 6 illustrates one example of a technique for embedding imagery in video.

FIG. 6 illustrates an example of a technique for providing video with personalized media. According to various embodiments, personalized media such as personalized imagery is embedded or provided as an overlay on video so that the personalized image is only discernible when the video is being viewed at an accelerated rate such as during fast forward or rewind. In other embodiments, personalized media is embedded or provided as an overlay on video so that it is viewable when the video is played at normal rates. At 601, profile and/or preference information is received. According to various embodiments, the name of a viewer is identified. In particular embodiments, the age, gender, income level, and/or interests of a viewer are identified. At 603, an image and placement parameters are selected. According to various embodiments, profile and/or preference information is used to select the image and placement parameters associated with media such as text or an image. For example, an image associated with the viewer's interest may be selected and placed near the bottom of a screen in particular colors. The selected image may be text, graphics, or other data. In some instances, multiple images can be selected for a single video. The multiple images may also be selected frames of another video.

At 605, the image is divided into portions. According to various embodiments, a subset of image pixels are selected for each image portion, so that a sequence of image portions would include substantially all of the image pixels. In particular embodiments, the number of subsets of image pixels generated is equal to the standard accelerated fast forward or rewind rate. For example, if the standard fast forward rate is 4x, four subsets of image pixels are generated where each subset includes approximately one quarter of the total image pixels. In another example, eight subsets of image pixels are generated where each subset include approximately one sixth of the total image pixels. Survey based and neuro-response based feedback can be used to select the number of subsets generated and the percentage of total image pixels to include in each subset. In some embodiments, the image is embedded or placed as an overlay on the video without any division into portions. The image can then be viewed when the video is played at normal rates.

At 607, video is received and decoded. The video may include intra-coded frames as well as predictive frames. In other examples, the video is analog video and may not require decoding. At 609, video frames are blended with image portions. In some examples, only intra-coded frames are blended with image portions and predictive frames remain unchanged. Hue, saturation, and value, etc. of image portion pixels may be blended with surrounding video pixels. Value may be associated with brightness and intensity or contrast. According to various embodiments, hue relates to different dominant wavelengths of light, such as red, purple, blue, etc.

The way a viewer perceives color may also vary along other dimensions. One of the dimensions is value, or lightness and darkness. In terms of a spectral definition of color, value describes the overall intensity or strength of the light. Another dimension is saturation. Saturation refers to the dominance of hue in the color. Desaturated colors constitute different scales of gray, running from white to black. Individual pixels in the plurality of image portions may be adjusted for hue, saturation, and value in order to blend the image effectively. At 611, video may be encoded.

The size, type, location of images as well as the amount of blending to use can be determined for particular images and video using survey based and neuro-response based feedback.

Figure 7:
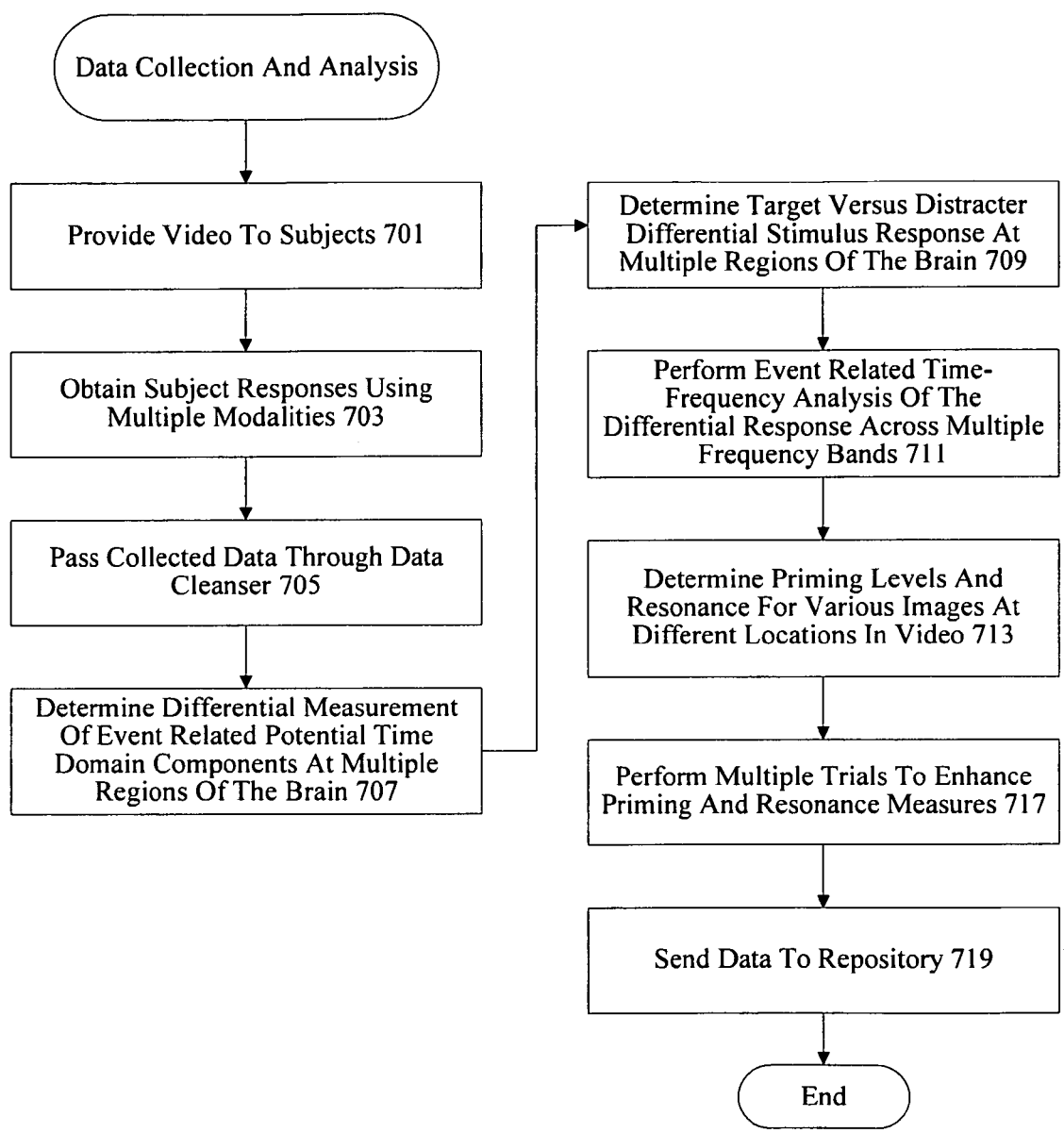
FIG. 7 illustrates one example of technique for performing data analysis for video personalized imagery.

FIG. 7 illustrates one example of using neuro-response based feedback for providing personalized media in video. At 701, stimulus material is provided to multiple subjects or to a particular individual. The multiple subjects may have particular profiles that match categories of viewers. According to various embodiments, stimulus includes streaming video and audio. In particular embodiments, subjects view stimulus in their own homes in group or individual settings. In some examples, verbal and written responses are collected for use without neuro-response measurements. In other examples, verbal and written responses are correlated with neuro-response measurements. At 703, subject neuro-response measurements are collected using a variety of modalities, such as EEG, ERP, EOG, GSR, etc. At 705, data is passed through a data cleanser to remove noise and artifacts that may make data more difficult to interpret. According to various embodiments, the data cleanser removes EEG electrical activity associated with blinking and other endogenous/exogenous artifacts.

According to various embodiments, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis. In particular embodiments, a stimulus attributes repository is accessed to obtain attributes and characteristics of the stimulus materials, along with purposes, intents, objectives, etc. In particular embodiments, EEG response data is synthesized to provide an enhanced assessment of effectiveness. According to various embodiments, EEG measures electrical activity resulting from thousands of simultaneous neural processes associated with different portions of the brain. EEG data can be classified in various bands. According to various embodiments, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present invention recognize that analyzing high gamma band (kappa-band: Above 60 Hz) measurements, in addition to theta, alpha, beta, and low gamma band measurements, enhances neurological attention, emotional engagement and retention component estimates. In particular embodiments, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various embodiments, high gamma waves (kappa-band) above 80 Hz (typically detectable with sub-cranial EEG and/or magnetoencephalograophy) can be used in inverse model-based enhancement of the frequency responses to the stimuli.

Various embodiments of the present invention recognize that particular sub-bands within each frequency range have particular prominence during certain activities. A subset of the frequencies in a particular band is referred to herein as a sub-band. For example, a sub-band may include the 40-45 Hz range within the gamma band. In particular embodiments, multiple sub-bands within the different bands are selected while remaining frequencies are band pass filtered. In particular embodiments, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various embodiments, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various embodiments, data from a specific modality can be enhanced using data from one or more other modalities. In particular embodiments, EEG typically makes frequency measurements in different bands like alpha, beta and gamma to provide estimates of significance. However, the techniques of the present invention recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various embodiments, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various embodiments, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various embodiments, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular embodiments, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various embodiments, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular embodiments, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various embodiments, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various embodiments, facial emotion encoding uses templates generated by measuring facial muscle positions and movements of individuals expressing various emotions prior to the testing session. These individual specific facial emotion encoding templates are matched with the individual responses to identify subject emotional response. In particular embodiments, these facial emotion encoding measurements are enhanced by evaluating inter-hemispherical asymmetries in EEG responses in specific frequency bands and measuring frequency band interactions. The techniques of the present invention recognize that not only are particular frequency bands significant in EEG responses, but particular frequency bands used for communication between particular areas of the brain are significant. Consequently, these EEG responses enhance the EMG, graphic and video based facial emotion identification.

According to various embodiments, post-stimulus versus pre-stimulus differential measurements of ERP time domain components in multiple regions of the brain (DERP) are measured at 707. The differential measures give a mechanism for eliciting responses attributable to the stimulus. For example the messaging response attributable to an advertisement or the brand response attributable to multiple brands is determined using pre-resonance and post-resonance estimates At 709, target versus distracter stimulus differential responses are determined for different regions of the brain (DERP). At 711, event related time-frequency analysis of the differential response (DERPSPs) are used to assess the attention, emotion and memory retention measures across multiple frequency bands. According to various embodiments, the multiple frequency bands include theta, alpha, beta, gamma and high gamma or kappa. At 713, priming levels and resonance for various products, services, and offerings are determined at different locations in the stimulus material. In some examples, priming levels and resonance are manually determined. In other examples, priming levels and resonance are automatically determined using neuro-response measurements. According to various embodiments, video streams are modified with different inserted advertisement images for various products and services to determine the effectiveness of the inserted advertisement images based on priming levels and resonance of the source material.

At 717, multiple trials are performed to enhance priming and resonance measures. In some examples, stimulus. In some examples, multiple trials are performed to enhance resonance measures.

In particular embodiments, the priming and resonance measures are sent to a priming repository 719. The priming repository 719 may be used to automatically select images for insertion into video.

Figure 8:
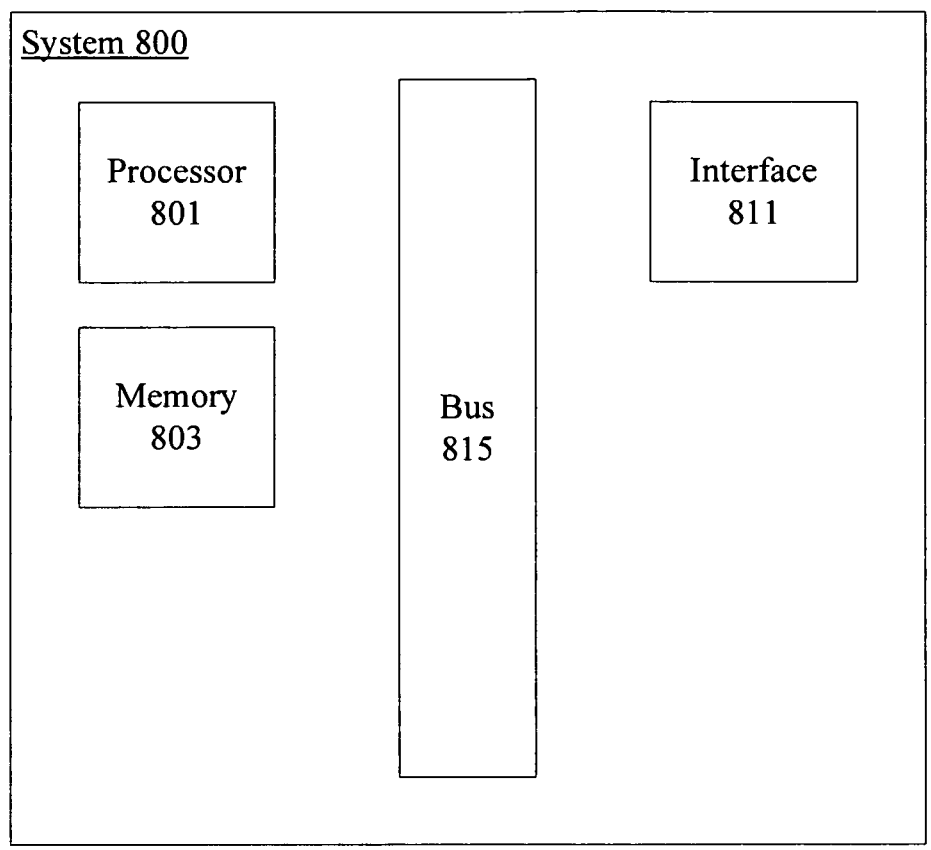
FIG. 8 provides one example of a system that can be used to implement one or more mechanisms.

According to various embodiments, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system. FIG. 8 provides one example of a system that can be used to implement one or more mechanisms. For example, the system shown in FIG. 8 may be used to implement an video embedded imagery system.

According to particular example embodiments, a system 800 suitable for implementing particular embodiments of the present invention includes a processor 801, a memory 803, an interface 811, and a bus 815 (e.g., a PCI bus). When acting under the control of appropriate software or firmware, the processor 801 is responsible for such tasks such as pattern generation. Various specially configured devices can also be used in place of a processor 801 or in addition to processor 801. The complete implementation can also be done in custom hardware. The interface 811 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

According to particular example embodiments, the system 800 uses memory 803 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present invention relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A method, comprising:
selecting media comprising a plurality of pixels;
dividing the pixels into a plurality of portions, each of the portions having a subset of the pixels, a first of the portions having a different set of the pixels than a second of the portions;
blending the first portion with a first frame of a video; and
blending the second portion with a second frame of the video such that the media is discernible when the video is played at a fast forward rate faster than a normal playback rate.

2. The method of claim 1, wherein the rate is four times the normal rate.

3. The method of claim 1, wherein dividing the media into a plurality of media portions comprises dividing the media into a number of media portions based on an average fast forward rate.

4. The method of claim 1, wherein the media comprises a name of the viewer.

5. The method of claim 1, wherein the blending the first media portion comprises adjusting at least one of a hue, a saturation or a value of the first media portion.

6. The method of claim 1, wherein the viewer of the video is asked to indicate if the media is discernible.

7. The method of claim 1, further comprising analyzing survey data to determine whether the media is discernible.

8. The method of claim 1, wherein the first media portion blended with the first frame and the second media portion blended with the second frame collectively form an advertisement that is only viewable during a fast forward or a rewind.

9. The method of claim 1 further comprising personalizing the media based on automatically compiled viewing characteristics.

10. The method of claim 1, further comprising selecting a location placement of the media in the video based on viewer preference data, the selecting of the media being based on the viewer preference data.

11. The method of claim 1, wherein dividing the pixels into the plurality of portions comprises randomly selecting the subsets of pixels.

12. The method of claim 1, wherein dividing the pixels into the plurality of portions comprises intelligently selecting the subsets of pixels.

13. The method of claim 1, wherein the subsets collectively include substantially all of the pixels of the media.

14. The method of claim 1, wherein the number of subsets equals an expected accelerated fast forward rate.

15. The method of claim 1, wherein the fast forward rate is x and each subset includes 1/x the total number of pixels in the media.

16. The method of claim 1, wherein the fast forward rate is x frames per second and a number of the subsets is x.

17. The method of claim 1, wherein the number of subsets is eight and each subset includes approximately one-sixth the total number of pixels in the media.

18. The method of claim 1, wherein at least some of the pixels of the subsets are adjusted for at least one of hue, saturation or value to blend the at least some of the pixels in the video.

19. The method of claim 1 further comprising analyzing neuro-response data collected from the viewer while exposed to the video with the media playing at one or more of the fast forward rate or the normal playback rate to determine if the media is discernible.

20. The method of claim 19, wherein the neuro-response data is collected using electroencephalography and electrooculography.

21. The method of claim 19 further comprising determining a presentation characteristic of the media based on the neuro-response data.

22. The method of claim 21, wherein the presentation characteristic comprises at least one of a clarity, an opacity or a contrast of the media relative to the video.

23. The method of claim 1, wherein the blending of the second media portion comprises adjusting at least one of a hue, a saturation or a value of the second media portion.

24. The method of claim 1, wherein the fast forward rate is an average fast forwarding rate, a multiple of the average fast forward rate, or a factor of the average fast forward rate.

25. The method of claim 1, wherein the media is not discernible when the video is played at the normal playback rate.

26. A system, comprising:
a selector to select media having a plurality of pixels; and
an encoder to:
divide the pixels into a plurality of portions, each of the portions including a subset of the pixels, a first of the portions having a different set of the pixels than a second of the portions, blend the first portion with a first frame of a video, and
blend the second portion with a second frame of the video such that the media is discernible when the video is played at a rate different than a normal playback rate.

27. The system of claim 26, wherein the rate is faster than the normal playback rate.

28. The system of claim 27, wherein the rate is at least one of a fast forward rate or a rewind rate.

29. The system of claim 26, further comprising a data analyzer to determine whether the media is discernible when the video is played at the normal rate.

30. The system of claim 26, wherein the encoder is to divide the media into the plurality of media portions based on the rate.

31. The system of claim 26, wherein the encoder is to adjust at least one of a hue, a saturation or a value of the plurality of portions.

32. The system of claim 26 further comprising a data analyzer to analyze survey data to determine whether the media is discernible.

33. The system of claim 26, wherein the media is personalized based on automatically compiled viewing characteristics.

34. The system of claim 26, wherein viewer preference data is used to select the media and to select a placement location of the media in the video.

35. The system of claim 7 further comprising a data analyzer to analyze neuro-response data collected from a viewer while exposed to the video with the media playing at one or more of the rate or the normal playback rate to determine if the media is discernible.

36. The system of claim 26, wherein the media is not discernible when the video is played at the normal playback rate.

37. A tangible machine readable storage device or storage disc comprising machine readable instructions which, when read, cause a machine to at least:
divide media comprising a plurality of pixels into a plurality of portions, each of the portions including less than all of the pixels, a first of the portions having a different set of the pixels than a second of the portions;
blend the first portion with a first frame of a video; and
blend the second portion with a second frame of the video such that the media is discernible when the video is played at a fast forward rate faster than a normal playback rate but is not discernible when the video is played at the normal playback rate.

38. The storage device or storage disc of claim 37, wherein the fast forward rate is approximately four times the normal rate.

39. The storage device or storage disc of claim 37, wherein the instructions cause the machine to divide the media into a number of portions based on the fast forward rate.

40. The storage device or storage disc of claim 37, wherein the media comprises a name of the viewer.

41. The storage device or storage disc of claim 37, wherein the instructions cause the machine to adjust at least one of a hue, a saturation or a value of the plurality of portions.

42. The storage device or storage disc of claim 37, wherein the instructions cause the machine to personalize the media based on automatically compiled viewing characteristics.

43. The storage device or storage disc of claim 37, wherein the instructions cause the machine to both select the media and a placement location of the media in the video based on viewer preference data.

44. The storage device or storage disc of claim 37, wherein the instructions cause the machine to analyze neuro-response data collected from a viewer while exposed to the video with the media playing at one or more of the fast forward rate or the normal playback rate to determine if the media is discernible.

45. The storage device or storage disc of claim 37, wherein the media is not discernible when the video is played at the normal playback rate.

46. A method, comprising:
dividing an image having a plurality of pixels into a plurality of portions, each of the portions comprising a subset of pixels, each subset being fewer than all the pixels in the plurality, a first of the portions having a different set of the pixels than a second of the portions;
blending the first portion with a first frame of a video; and
blending the second portion with a second frame of the video such that the image is discernible when the video is played at a rate different than a normal playback rate.

* * * * *